US009775538B2

(12) United States Patent
Eichler

(10) Patent No.: US 9,775,538 B2
(45) Date of Patent: Oct. 3, 2017

(54) SYSTEM AND METHOD FOR DETERMINING THE POSITION OF THE TIP OF A MEDICAL CATHETER WITHIN THE BODY OF A PATIENT

(75) Inventor: Uzi Eichler, Haifa (IL)

(73) Assignee: MediGuide Ltd., Haifa (IL)

(*) Notice: Subject to any disclaimer, the term of this patent is extended or adjusted under 35 U.S.C. 154(b) by 1693 days.

(21) Appl. No.: 13/130,377

(22) PCT Filed: Dec. 3, 2009

(86) PCT No.: PCT/US2009/066653
§ 371 (c)(1),
(2), (4) Date: May 20, 2011

(87) PCT Pub. No.: WO2010/065786
PCT Pub. Date: Jun. 10, 2010

(65) Prior Publication Data
US 2011/0230758 A1 Sep. 22, 2011

Related U.S. Application Data

(60) Provisional application No. 61/119,502, filed on Dec. 3, 2008.

(51) Int. Cl.
*A61B 5/05* (2006.01)
*A61B 6/00* (2006.01)
(Continued)

(52) U.S. Cl.
CPC ............ *A61B 5/06* (2013.01); *A61B 5/062* (2013.01); *A61B 5/6852* (2013.01); *A61B 5/743* (2013.01);
(Continued)

(58) Field of Classification Search
USPC ....................................................... 600/424
See application file for complete search history.

(56) References Cited

U.S. PATENT DOCUMENTS 6,275,724 B1 8/2001 Dickinson et al.
2002/0049375 A1* 4/2002 Strommer et al. ............ 600/407
(Continued)

FOREIGN PATENT DOCUMENTS

WO 03/092488 11/2003
WO 2006/043276 4/2006
(Continued)

OTHER PUBLICATIONS

Author: Lengyel, Jed Title: Time-Dependent Three-Dimensional Intravascular Ultrasound Citation: Computer Graphics Proceedings, Los Angeles, IEEE Reference pp. 457-464 Publication Date: Aug. 6, 1995.
Author: Jourdain, Melissa Title: 3D reconstruction of an IVUS transducer trajectory with a signle view in cineangiography Citation: Proceedings of SPIE, vol. 5747 Reference Pages: Abstract Publication Date: Apr. 29, 2005.

*Primary Examiner* — Patricia Park
(74) *Attorney, Agent, or Firm* — Dykema Gossett PLLC

(57) ABSTRACT

Method and system for determining the current position of a selected portion of a medical catheter inserted into a tubular organ (118) of the body of a patient, the method comprising the procedures of inserting a medical positioning system (MPS) (102) catheter into the tubular organ (118), acquiring a plurality of mapping positions (120) within the tubular organ (118), displaying a mapping position (120) representation of the mapping positions (120), constructing a mapping path (122) according to the mapping positions (120), inserting the medical catheter into the tubular organ (118) until the selected portion reaches the initial position, displaying an operational image of the tubular organ (118), a path representation of the mapping path (122), and an initial position representation of the initial position superimposed on the operational image, registering the selected portion with the initial position, measuring a traveled length of the medical catheter within the tubular organ (118) from the initial position, and estimating the current position.

22 Claims, 12 Drawing Sheets

(51) Int. Cl.
  *A61B 5/06* (2006.01)
  *A61B 5/00* (2006.01)
  *A61B 8/12* (2006.01)
  *A61B 8/00* (2006.01)
  *A61B 8/08* (2006.01)
  *A61B 34/20* (2016.01)
  *A61M 25/01* (2006.01)
  *A61B 6/12* (2006.01)
(52) U.S. Cl.
  CPC .............. *A61B 6/5247* (2013.01); *A61B 8/12* (2013.01); *A61B 8/4245* (2013.01); *A61B 8/4254* (2013.01); *A61B 8/5238* (2013.01); *A61B 34/20* (2016.02); *A61B 6/12* (2013.01); *A61B 6/504* (2013.01); *A61B 2034/2051* (2016.02); *A61M 25/0108* (2013.01)

(56) References Cited

U.S. PATENT DOCUMENTS

| | | |
|---|---|---|
| 2003/0220557 A1 | 11/2003 | Cleary et al. |
| 2004/0147837 A1 | 7/2004 | Macaulay et al. |
| 2006/0058647 A1* | 3/2006 | Strommer et al. ............ 600/434 |
| 2009/0310847 A1 | 12/2009 | Matsuzaki et al. |

FOREIGN PATENT DOCUMENTS

| | | | |
|---|---|---|---|
| WO | 2008/062358 | | 5/2008 |
| WO | WO2008/062358 | * | 5/2008 |

* cited by examiner

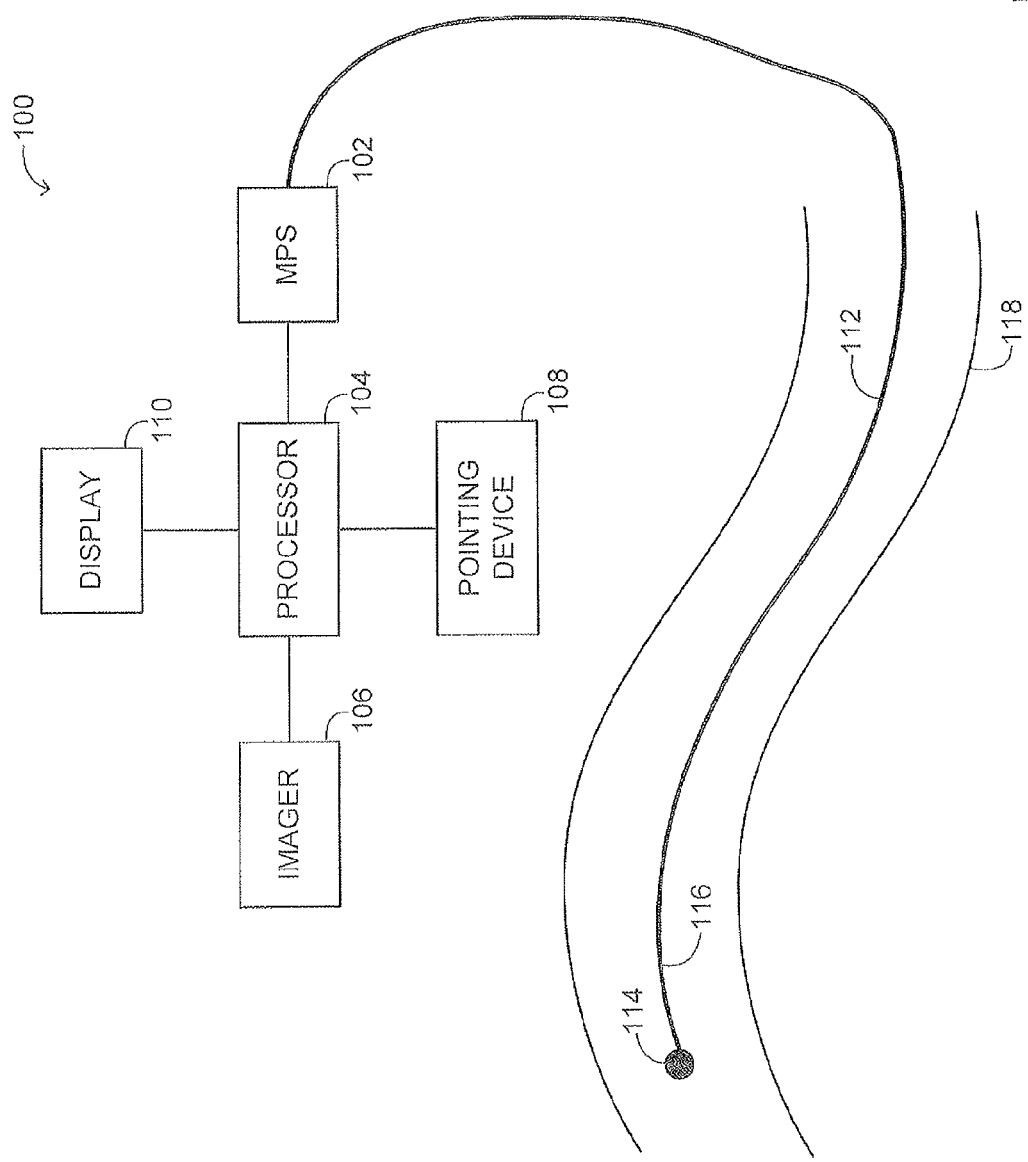

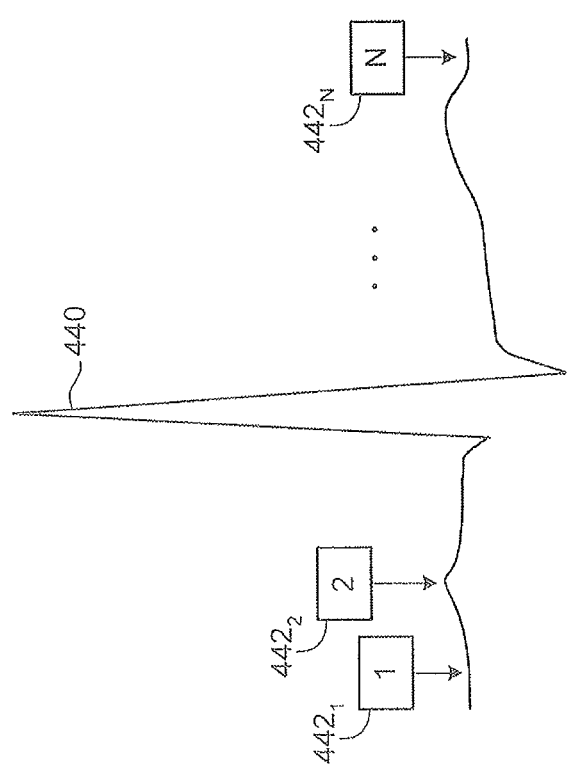

SYSTEM AND METHOD FOR DETERMINING THE POSITION OF THE TIP OF A MEDICAL CATHETER WITHIN THE BODY OF A PATIENT

CROSS-REFERENCE TO RELATED APPLICATIONS

This application claims the benefit of U.S. provisional application No. 61/119,502, filed 3 Dec. 2008, which is hereby incorporated by reference as though fully set forth herein.

FIELD OF THE DISCLOSED TECHNIQUE

The disclosed technique relates to medical devices in general, and to methods and systems for determining the position and orientation of the tip of a catheter, in particular.

BACKGROUND OF THE DISCLOSED TECHNIQUE

Cardiac operations, such as angioplasty, stent deployment and ablation can be performed in a minimally invasive surgery (MIS) setting, by employing a catheter of the appropriate type. A surgeon, who performs a MIS, needs to observe the position and orientation of the tip of the catheter, continuously, in order to navigate the catheter to a desired location within the heart of the patient.

Methods and systems for determining the position and orientation of the tip of a catheter are known in the art. For example, such systems employ an electromagnetic sensor mounted at the tip of the catheter, and a medical positioning system (MPS), to determine the position and orientation of the tip of the catheter, according to an output of the electromagnetic sensor. The MPS determines the position of the tip of the catheter, within a vessel of the heart, where images are acquired by an invasive medical imager, from inside of the vessel.

One example of invasive medical imagers is an intravascular ultrasound (IVUS) imager, which is located at the tip of an IVUS catheter, to produce a plurality of images from inside the vessel. The IVUS imager employs an ultrasonic transducer at a tip of the IVUS catheter, to acquire the images. The IVUS catheter is inserted into the vessel, and advanced toward a region of interest within the body of the patient. The IVUS imager acquires a plurality of ultrasonic images during pull-back of the catheter from the region of interest, while the MPS detects the position of the tip of the IVUS catheter with respect to each of the ultrasonic images. A processor, which is connected with the IVUS imager and with the MPS, produces a video image of the inside of the vessel, according to the ultrasonic images, and the detected positions of the tip of the IVUS catheter. The IVUS catheter is employed in diagnosis and treatment of different diseases, such as atheroma, arteriosclerosis, and as an adjunct to balloon angioplasty and in guiding stent deployment.

U.S. Pat. No. 6,246,898 B1 issued to Vesely et al. and entitled "Method for Carrying out a Medical Procedure Using a Three-dimensional Tracking and Imaging System" is directed to a method for tracking the position and motion of a catheter, by employing a three-dimensional (3-D) tracking and imaging system. The 3-D tracking and imaging system includes a plurality of mobile transducers, a plurality of reference transducers, a computer system, an instrument, and an optional robotics subsystem. The computer system includes a 3-D tracking system, an imaging modality system, an image registration system, an image warping system and geometry transformation system, a user interface, and a display. The optional robotics subsystem includes a robotics control system and a robotic manipulator system. The instrument is a diagnostic tool such as a catheter. The robotics control subsystem controls the robotic manipulator system, which physically moves the instrument.

The mobile transducers are fitted onto the instrument. The reference transducers are mounted to locations on the patient in strategic reference locations. The imaging modality system acquires 4-D image data from a magnetic resonance imager (MRI). The position and movement of the instrument is tracked by the 3-D tracking system. The 3-D tracking system employs triangulation algorithms to determine the relative spatial coordinates of a combination of two transducers according to the time-of-flight principle of ultrasonic waves. The image registration system registers the position of the instrument with the corresponding spatial coordinates within the acquired images, provided by the imaging modality system. The image warping and geometry transformation system warps the image data to compensate for the changes that occurred in the period of time between image acquisition and surgery. The user interface enables user interaction with the computer system and the display displays the images provided by the image registration system.

An article by Jourdain, Mélissa et al. "3D Reconstruction of an IVUS Transducer Trajectory with a Single View Cineangiography." *Medical Imaging* 2005: *Image Processing, Proc. of SPIE* 5747 (2005) is directed to a method for determining the three-dimensional trajectory of an IVUS transducer during an intervention by utilizing a single X-ray image and using a pullback distance of the ultrasound transducer as a priori information.

The method employs two imaging modalities, IVUS imaging and X-ray imaging. The IVUS imaging modality produces a sequence of cross-sectional images of a lumen within the body of a patient and the X-ray imaging modality produces a single-view X-ray image sequence. The method employs a single-plane model, a trajectory pruning technique and a tracking algorithm. The single-plane model utilizes a full perspective camera model and the knowledge of a pullback distance of a catheter inserted within a lumen of the body of a patient. The full perspective camera model is used as a basis for computing the projection of the position of the IVUS transducer in an X-ray plane. The trajectory pruning technique employs a cost function, and considers possible trajectories of the IVUS transducer on the X-ray plane. These possible trajectories are partly based on the curvature of the lumen. The cost function assigns specific weights to the solutions of possible trajectories based on the number of turns in the trajectory of the catheter.

The starting position of the IVUS transducer is inputted into the tracking algorithm. The tracking algorithm tracks the IVUS transducer by employing an image-differencing method (i.e., changes in pixel intensity) between consecutive frames in the image sequence. A 3-D position of the catheter is retrieved based on its previously-known position, outputted by the tracking algorithm, and with the known pullback distance of the catheter.

U.S. Pat. No. 5,724,978 issued to Tenhoff, entitled "Enhanced Accuracy of Three-dimensional Intraluminal Ultrasound (ILUS) Image Reconstruction" is directed to a method and apparatus for imaging an organ in a body of a patient, in order to obtain a three-dimensional image reconstruction from an acquired set of echographic data. The apparatus includes an ultrasound imaging catheter system and a catheter tracking system. The ultrasound imaging system employs a conventional intraluminal catheter with an imaging tip. The tracking system includes an ultrasound transducer. The ultrasound transducer is mounted adjacent to the imaging tip of the catheter. The imaging tip of the catheter acquires echographic images.

The catheter is inserted into the body of the patient and advanced into a required region of interest. The ultrasound transducer acquires an echographic data set (i.e., a sequence of 2-D images) within the region of interest during a pull-back procedure of the catheter. The tracking system tracks the position of the ultrasound transducer. The position of the ultrasound transducer with respect to each echographic data set at each point, during image acquisition along the pull-back path of the catheter, is calculated by determining a tangent to the catheter centerline of the ultrasound transducer, at each of the respective locations where the echographic data sets are acquired. The calculated position of the catheter is used to determine a three-dimensional pull-back trajectory of the catheter. The acquired sequence of the 2-D images is stacked in order to generate a 3-D reconstruction from the ultrasound images. Non-linear paths of the catheter are taken into account to avoid errors in the 3-D image reconstruction.

U.S. Pat. No. 6,148,095 issued to Prause et al., entitled "Apparatus and Method for Determining Three-dimensional Representations of Tortuous Vessels" is directed to an apparatus and a method for three-dimensional reconstructions of tortuous vessels employing IVUS and data fusion with biplane angiography. The apparatus includes a biplane angiographic unit, an IVUS imaging unit, a data fusion unit, and a display unit. The IVUS imaging unit includes a catheter. The data fusion unit includes a 3-D pullback path determination unit, a catheter twist determination unit, a correlation unit, an interpolation unit, and a phase correlation unit. The biplane angiographic unit and the IVUS imaging unit are connected to the data fusion unit. The display unit is connected to the data fusion unit.

The method includes the steps of initialization, image acquisition, centerline reconstruction, IVUS segmentation, data fusion and evaluation. The data fusion step includes the steps of catheter detection in 3-D, reconstruction of the 3-D pullback path, calculation of catheter twist, mapping, interpolation and rendering a quantitative analysis.

The biplane angiographic unit is calibrated in the initialization step. Image acquisition is performed by the biplane angiographic unit that acquires angiograms of the tortuous vessel, and the IVUS imaging unit that acquires IVUS images via catheter pullback from the tortuous vessel. The phase correlation unit uses the heart beat or the breathing cycle of the patient to ensure that the images acquired from the IVUS catheter are obtained under consistent conditions. The centerline of the vessel is reconstructed from a biplane angiogram. The acquired IVUS pullback images are then segmented. In the data fusion step, data fusion between biplane angiography and an IVUS pullback imaging is employed. Catheter detection in 3-D is performed using 3-D data derived from angiographic projection images. The 3-D pullback path determination unit determines a pullback path of the catheter from the acquired biplane angiograms, by employing a spline-based 3-D minimization approach.

The catheter twist determination unit determines a tortuosity-induced twist of the catheter. The correlation determination unit maps the captured IVUS image slices to the 3-D pullback path, according to a pullback speed and the determined tortuosity-induced twist. In the interpolation step, the centerline is approximated by Bezier curves. Borders between consecutive 2-D IVUS slices are interpolated and the IVUS slices are swept along Bezier-approximated vessel centerlines in order to generate the 3-D vessel reconstruction. The display unit displays quantitative representations of the IVUS images, angiograms and 3-D representations of the vessel.

US Patent Application Publication No. US 2006/0058647 A1 to Strommer et al., entitled "Method and System for Delivering a Medical Device to a Selected Position within a Lumen" is directed to a system and method employing graphically assisted medical positioning and imaging, for positioning a medical device within a lumen of the body of a patient.

The system includes a medical positioning system (MPS), an MPS catheter, two-dimensional image acquisition devices, a graphical user interface (GUI), and a processor. The catheter includes an MPS sensor at its tip. The processor is coupled with the GUI and with the MPS.

A stent which is to be deployed within the lumen is coupled with the catheter. An operator visually navigates the medical device by maneuvering it through the lumen toward a selected position. The position of the moving catheter within the lumen, as determined by the MPS, is associated with a three-dimensional coordinate system and is further associated with a respective activity state of an organ of the patient. IVUS images are acquired during the pull-back of the catheter from within the lumen. The lumen is externally imaged by a two-dimensional image acquisition device. The processor reconstructs three-dimensional images from the two-dimensional images acquired by the two-dimensional image acquisition device according to the organ timing signal of the organ. The trajectory of the catheter, detected by the MPS is superimposed on the three-dimensional images. The GUI displays a representation of the medical device on the three-dimensional image of the lumen.

An article by Slager, Cornelius J. et al. "True 3-Dimensional Reconstruction of Coronary Arteries in Patients by Fusion of Angiography and IVUS (ANGUS) and Its Quantitative Validation." Circulation Journal of the American Heart Association 102 (2000): 511-516 is directed to a method for three-dimensional image reconstruction of coronary arteries by fusing angiographic and IVUS information. The method employs two imaging modalities: IVUS, which generates IVUS image cross sections and X-ray, which generates X-ray images. The method employs a motorized stepped pullback of a sheath-based catheter in order to acquire IVUS images, during an R-wave—triggered mode in a cardiac cycle. The method includes the steps of acquisition of a set of biplane angiographic (i.e., X-ray) images, acquisition of IVUS images, processing of X-ray and ultrasound images, 3-D reconstruction of a catheter centerline (i.e., coreline), and repositioning of the IVUS image cross sections on a reconstructed pullback trajectory. The method employs a wire model and a gutter model. Both the wire model and the gutter model estimate the length of the 3-D reconstructed catheter centerline.

The processing of the X-ray images includes the step of 3-D reconstruction of the catheter centerline and determining the borders of the lumen. The processing of the ultrasound images includes the step of determining the borders in the IVUS images, by employing a contour detection program. The 3-D reconstruction of the catheter centerline entails firstly, the direct 3-D reconstruction of the distal and proximal points of the centerline. Secondly, the centerline reconstruction between the distal and proximal points is approximated by employing a 3-D circular segment, which is adapted three dimensionally in a stepwise manner. The acquired set of biplane angiographic images record the 3-D position of the catheter and a 3-D pullback trajectory is consequently predicted.

Contours of the lumen obtained from the IVUS images are fused with the 3-D pullback trajectory of the catheter. Based on the reconstructed catheter centerline, the IVUS image cross sections are positioned on a reconstructed trajectory. The acquired IVUS image cross sections are distributed at equidistant intervals on the reconstructed catheter centerline and an angular rotation of the reconstructed IVUS image cross sections is determined. The reconstruction further entails the IVUS image cross sections to be angularly rotated around the 3-D pullback trajectory. The acquired biplane images are employed in optimization of the angular rotation of the reconstructed IVUS image cross sections. The pullback length which is determined according to the quantity of pullback steps is compared with the reconstructed path length, which is determined according to the wire model and the gutter model.

SUMMARY OF THE DISCLOSED TECHNIQUE

It is an object of the disclosed technique to provide a novel method and system for determining the current position of a selected portion (e.g., the tip) of a medical catheter within a tubular organ, according to the current distance traversed by the selected portion of the medical catheter from an initial position (e.g., an origin) of a path, previously traversed by a mapping catheter.

In accordance with the disclosed technique, there is thus provided a method for determining the current position of a selected portion of a medical catheter, inserted into a tubular organ of the body of a patient. The method includes the procedures of inserting a medical positioning system (MPS) catheter into the tubular organ where the MPS catheter includes an MPS sensor coupled with an MPS, acquiring a plurality of mapping positions within the tubular organ by the MPS, displaying a mapping position representation of the mapping positions superimposed on a pre-operational image of the tubular organ, constructing a mapping path according to the mapping positions where a selected one of these mapping positions is defined as an initial position of the mapping path, inserting the medical catheter into the tubular organ until the selected portion reaches the initial position, displaying an operational image of the tubular organ superimposed on the operational image such that the operational image includes a marker image of the tip of the medical catheter, a path representation of the mapping path, and an initial position representation of the initial position, registering the selected portion with the initial position, measuring a traveled length of the medical catheter within the tubular organ from the initial position, and estimating the current position according to the traveled length, the mapping positions, and according to a plurality of calculated distances between each of the mapping positions and the initial position, along the mapping path.

According to another aspect of the disclosed technique, there is thus provided a system for determining the position of the medical catheter within the tubular organ of the body of the patient. The system includes an MPS, an MPS catheter, a memory, a registerer, a traveled length detector, and a processor. The MPS includes at least one electromagnetic field generator, an MPS sensor, and an MPS processor. The MPS processor is coupled with at least one electromagnetic field generator, the memory, and with the MPS sensor. The MPS catheter is coupled with the MPS sensor. The processor is coupled with the memory, the registerer and with the traveled length detector. The traveled length detector is coupled with the medical catheter. The electromagnetic field generator generates an electromagnetic field. The MPS processor determines the relative position of the MPS sensor from at least one electromagnetic field generator, according to the electromagnetic field. The MPS catheter is inserted into the tubular organ to a plurality of physical points, for which the MPS processor determines respective mapping positions thereby defining a mapping path. One of the mapping positions is determined to be the initial position. The memory stores the mapping path. The register determines a registration situation of the selected portion of the medical catheter with the initial position. The traveled length detector measures the traveled length of the medical catheter within the tubular organ. The traveled length is defined as a length of the mapping path of the selected portion of the medical catheter, from the initial position. The processor estimates the current position of the selected portion of the medical catheter, according to the traveled length and according to calculated distance between the mapping positions, from the initial position along the mapping path.

BRIEF DESCRIPTION OF THE DRAWINGS

The disclosed technique will be understood and appreciated more fully from the following detailed description taken in conjunction with the drawings in which:

FIG. 1A is a schematic illustration of a system for producing a mapping path of a trajectory of an MPS catheter, within a tubular organ of the body of a patient, constructed and operative in accordance with an embodiment of the disclosed technique;

FIG. 4B is a schematic illustration of an organ timing signal of an organ of a patient and representative points in the organ timing signal;

DETAILED DESCRIPTION OF PREFERRED EMBODIMENTS

Figure 1B:
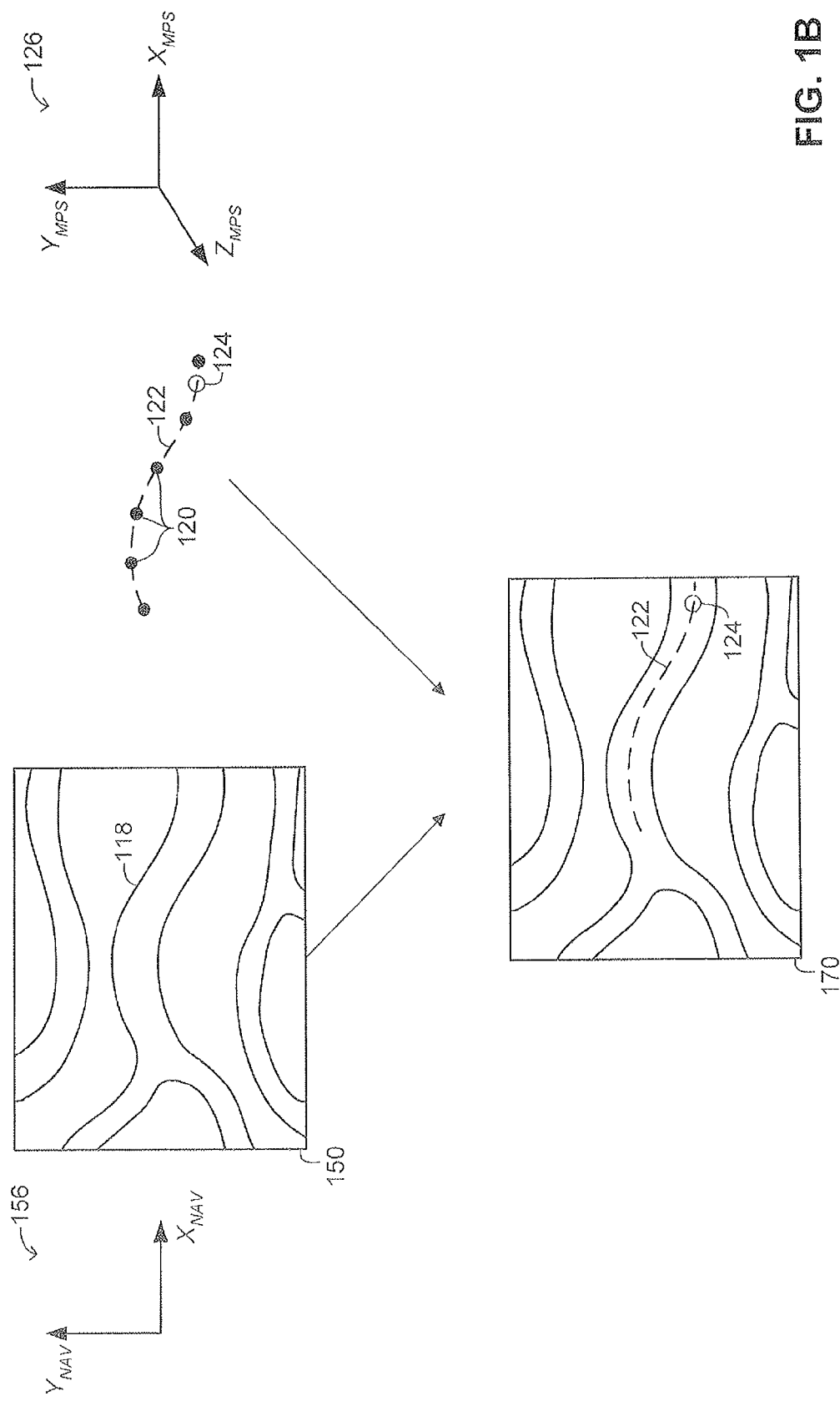
FIG. 1B is a schematic illustration of a superimposition of the mapping path of the trajectory of the MPS catheter of FIG. 1A, on an image of the tubular organ.

The disclosed technique overcomes the disadvantages of the prior art by employing a mapping catheter to map a path, traversed by the mapping catheter within a tubular organ, and registering a representation of the tip of a medical catheter with the origin of the path. Furthermore, the disclosed technique provides a system and method for determining the position of a selected portion (e.g., the tip) of the medical catheter within the tubular organ, according to the current distance of the tip of the medical catheter from an initial position (e.g., an origin) of the path. The mapping catheter includes an electromagnetic sensor located at the tip thereof, to detect the position of the tip along the path, with the aid of a Medical Positioning System (MPS). A processor superimposes a representation of the tip of the mapping catheter, on a two-dimensional image of the tubular organ, as a user (e.g., a surgeon, a medical practitioner, a technician) advances the mapping catheter within the tubular organ, to enable the user to navigate the mapping catheter through the tubular organ.

The processor constructs a mapping path of the path of the mapping catheter, according to different positions (i.e., mapping positions) of the tip of the mapping catheter along the path, and superimposes this mapping path on the two-dimensional image. At the commencement of the operation on a patient, the user registers the tip of the medical catheter with the origin of the mapping path. During the operation (e.g., a surgical procedure) on the patient, as the surgeon navigates the medical catheter within the tubular organ, a traveled length detector measures the traveled length of the tip of the medical catheter from the origin of the mapping path. The processor estimates the current position of the tip of the medical catheter, according to the traveled length of the tip of the catheter from the origin and according to a plurality of calculated distances between each of the mapping positions and the initial position, along the mapping path.

The processor can gate (i.e., synchronize) each of the mapping positions along the mapping path, with an activity state of an organ of the patient (e.g., the heart or the lungs), and produce a different mapping path corresponding to a different activity state of the organ. The processor can then direct a display to display the respective mapping path, according to the current activity state of the organ, by employing an organ timing monitor, such as an electrocardiogram (ECG), and the like. In this manner, the surgeon obtains a substantially stable image of the mapping path, against a real-time two-dimensional image of the tubular organ. Alternatively, the processor can superimpose the mapping path on a non-real-time image (i.e., a previously acquired image) of the tubular organ (e.g., a cine-loop), and direct the display to display the mapping path on this cine-loop.

The term "position" herein below, refers to the location of a point or point-like entity in space, the orientation of the point-like entity in space, or a combination thereof. The term "tubular organ" herein below, refers to a bodily organ, having an elongated tubular shape, such as a blood vessel, a vein, an artery, a heart cavity, (e.g., atrium or chamber), a substantially tubular or cylindrical object with non-zero internal volume, and the like. It is noted that the terms tubular organ, tubular organ, blood vessel, and artery, in the description herein below, are interchangeable.

The term "organ timing signal" herein below, refers to a signal representing the cardiac cycle of the heart of the patient, or a signal representing the respiratory cycle of the lungs of the patient. An organ timing signal can be acquired for example, by employing an ECG, or measuring the movements of the tubular organ due to cardiac or respiratory cycles, by an electromagnetic sensor. The term "cine-loop" herein below, refers to a prerecorded sequence of a set of two-dimensional images of the tubular organ, which are played back repetitiously (i.e., in a loop), in synchrony with the real-time organ timing signal of the inspected organ of the patient. It is noted that the terms "initial position" and "origin" are interchangeable throughout the description.

Reference is now made to FIGS. 1A and 1B. FIG. 1A is a schematic illustration of a system, generally referenced 100, for producing a mapping path of a trajectory of an MPS catheter, within a tubular organ of the body of a patient, constructed and operative in accordance with an embodiment of the disclosed technique. FIG. 1B is a schematic illustration of a superimposition of the mapping path of the trajectory of the MPS catheter of FIG. 1A, on an image of the tubular organ.

System 100 includes a Medical Positioning System (MPS) 102, a processor 104, an imager 106, a pointing device 108, a display 110, an MPS catheter 112, an MPS sensor 114 and a memory (not shown). MPS sensor 114 is located at a distal portion 116 of MPS catheter 112 (i.e., typically attached thereto). MPS 102 includes an electromagnetic field generator (not shown) for generating an electromagnetic field (not shown). It is noted that MPS 102 typically employs a plurality of electromagnetic field generators (not shown). MPS 102 further includes an MPS processor (not shown). Processor 104 is coupled with MPS 102, imager 106, pointing device 108, display 110 and with the memory. MPS 102 is coupled with MPS sensor 114, via an electric conductor. Alternatively, MPS 102 is coupled with MPS sensor 114 via a wireless link. The MPS processor is coupled with the plurality of electromagnetic field generators and with MPS sensor 114. MPS sensor 114 is in form of a coil, which produces an output in response to the electromagnetic field generated by the electromagnetic field generator. MPS 102 is a device which determines the position of distal portion 116 of MPS catheter 112, according to the output of MPS sensor 114. The MPS processor determines the relative position of MPS sensor 114 from the plurality of electromagnetic field generators, according to the electromagnetic field that is generated by each respective electromagnetic field generator.

Imager 106 acquires a pre-operative image 150 (FIG. 1B), of a tubular organ 118 of the body of a patient (not shown). Imager 106 is a two-dimensional image acquisition device, such as a fluoroscope, an ultrasound image detector, a C-arm, and the like. Alternatively, imager 106 is a three-dimensional image acquisition device, such as computer tomography (CT) imager, magnetic resonance imager (MRI), positron emission tomography (PET) imager, single photon emission computer tomography (SPECT) imager, ultrasound image detector, infrared image detector, X-ray imager, optical coherence tomography (OCT) imager, intracardiac echocardiogram (ICE), and the like. Pointing device 108 is a registerer, employed for determining a registration situation, and is typically a user interface, which can be for example, a computer mouse, a touch screen, a track-ball, and the like.

A three-dimensional coordinate system 126 (FIG. 1B) associated with MPS 102 is registered with a two-dimensional coordinate system 156 associated with pre-operational image 150. Alternatively, three-dimensional coordinate system 126 associated with registered with a two-dimensional coordinate system (not shown) associated with imager 106. During a mapping session (i.e., a pre-operational procedure), prior to an operation on the patient, a surgeon (not shown) inserts MPS catheter 112 into tubular organ 118, until distal portion 114 of MPS catheter 112 enters a field of view (i.e., FOV) of imager 106.

As the surgeon advances MPS catheter 112 into tubular organ 118, MPS 102 detects the position of distal portion 116 of MPS catheter 112, according to an output of MPS sensor 114. MPS 102 acquires a plurality of mapping positions 120 (FIG. 1B), respective of the positions of distal portion 116, during movement of MPS catheter 112 within tubular organ 118, toward a region of interest within the body of the patient. Alternatively, MPS 102 acquires mapping positions 120 during pull-back of MPS catheter 112, from the region of interest toward a point of entry (not shown) of MPS catheter 112 into tubular organ 118. MPS 102 registers each of mapping positions 120 with pre-operational image 150, such that each of mapping positions 120 is associated with a respective two-dimensional coordinate on pre-operational image 150.

Processor 104 constructs a mapping path 122 (i.e., an MPS trace), which is an approximate representation of the trajectory of the movement of MPS catheter 112, within tubular organ 118. Processor 104 constructs mapping path 122, according to the coordinates of each of mapping positions 120. The memory stores mapping path 122.

The surgeon determines an origin 124 (FIG. 1B) of mapping path 122. Origin 124 is a reference point, which can be for example, a point on mapping path 122, one of mapping positions 120, a physical point on the body of the patient (e.g., as marked by the surgeon), and the like. The surgeon selects origin 124 by employing pointing device 108. Processor 104 superimposes mapping path 122 on pre-operational image 150, thereby producing a superimposed pre-operational image 170. The registration between coordinate system 126 associated with MPS 102 and coordinate system 156 associated with pre-operational image 150 facilitates this superposition. Processor 104 directs display 110 to display superimposed pre-operational image 170.

Figure 2A:
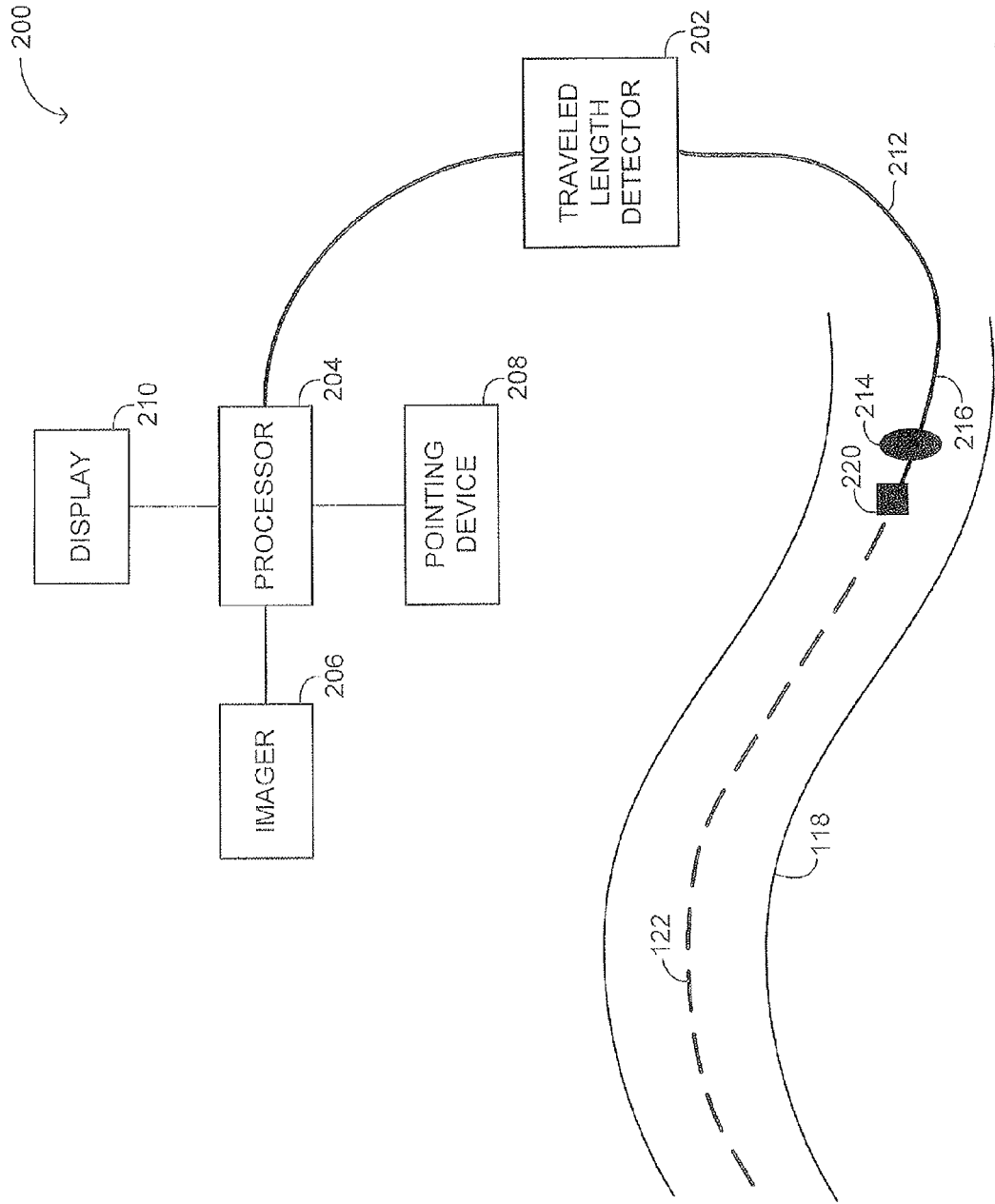
FIG. 2A is a schematic illustration of a system for determining the position of a medical catheter, within a tubular organ of a patient, constructed and operative in accordance with another embodiment of the disclosed technique.
Figure 2B:
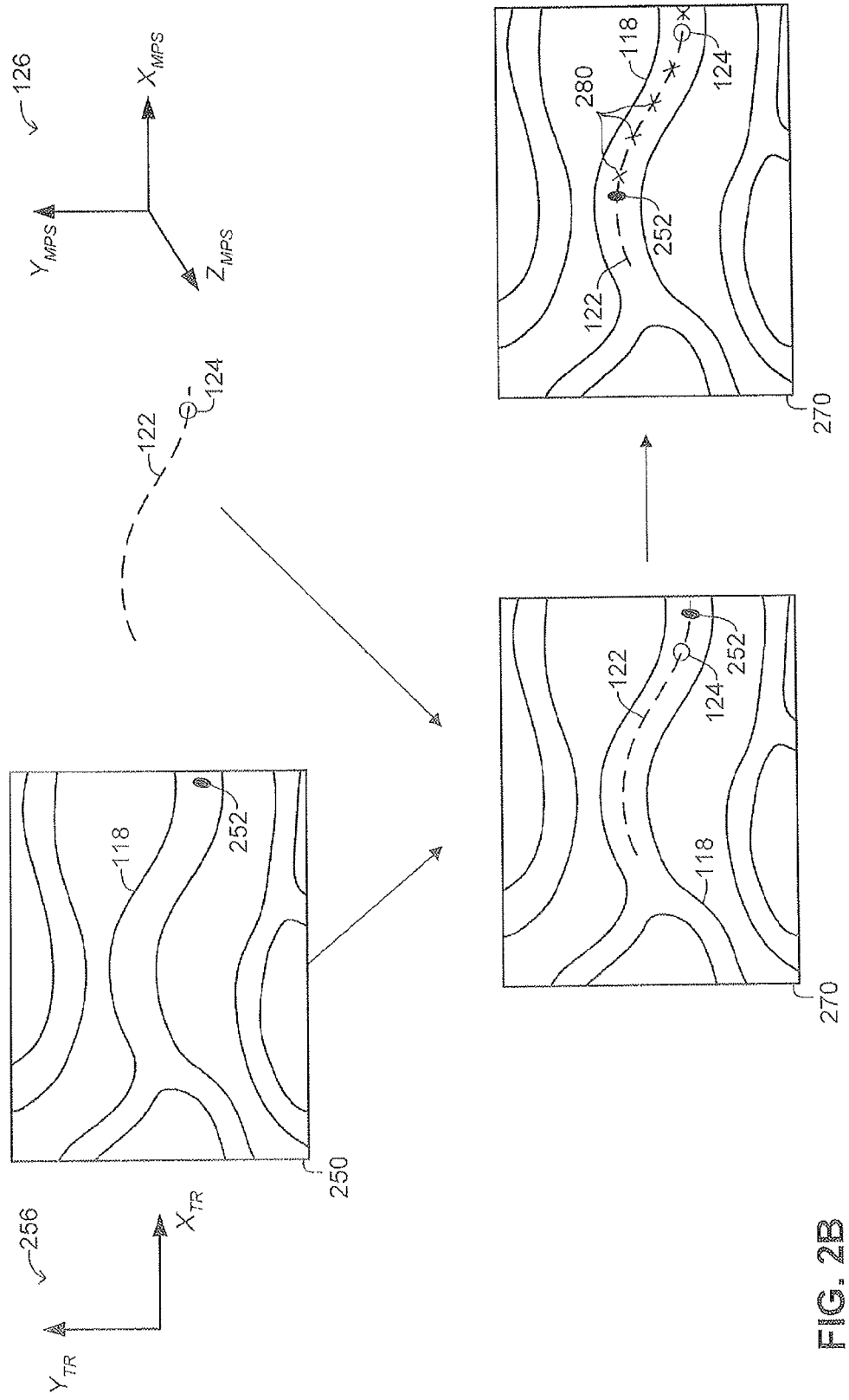
FIG. 2B is a schematic illustration of the mapping path of the trajectory of the MPS catheter of the system of FIG. 1A, superimposed on an image of the tubular organ of the patient.

Reference is now made to FIGS. 2A and 2B. FIG. 2A is a schematic illustration of a system, generally referenced 200, for determining the position of a medical catheter, within a tubular organ of a patient, constructed and operative in accordance with another embodiment of the disclosed technique. FIG. 2B is a schematic illustration of the mapping path of the trajectory of the MPS catheter of the system of FIG. 1A, superimposed on an image of the tubular organ of the patient.

System 200 includes a traveled length detector 202, a processor 204, an imager 206, a pointing device 208, a display 210, a medical catheter 212, a radiopaque marker 214, a memory (not shown), and an Intravascular Ultrasound (IVUS) imager 220. Radiopaque marker 214 and IVUS imager 220 are located at a distal portion 216 of medical catheter 212. Processor 204 is coupled with traveled length detector 202, imager 206, pointing device 208, display 210, and with the memory. Traveled length detector 202 is coupled with medical catheter 212. Processor 204, imager 206, pointing device 208, and display 210, are similar to processor 104, imager 106, pointing device 108, and display 110, respectively. Alternatively, processor 204, imager 206, pointing device 208, and display 210, are different than processor 104, imager 106, pointing device 108, and display 110, respectively.

Traveled length detector 202 is a device which measures the travel distance of medical catheter 212, relative to a selected point. Traveled length detector 202 can be for example, a fiber-optic interferometric system, electromechanical system utilizing an electric generator, variable electro-resistive device (e.g., a linear potentiometer, rotary potentiometer), and the like.

During operation on the body of the patient, the surgeon inserts medical catheter 212 into tubular organ 218 (i.e., after MPS catheter 112 is removed from tubular organ 218), until radiopaque marker 214 of medical catheter 212 is located within the FOV of imager 206. With reference to FIG. 2B, the surgeon advances medical catheter 212 into tubular organ 118, and imager 206 acquires an operational image 250 of tubular organ 118, until radiopaque marker 214 reaches origin 124. Three-dimensional coordinate system 126 associated with MPS 102 is registered with a two-dimensional coordinate system 256 associated with operational image 250. Alternatively, three-dimensional coordinate system 126 is registered with a two-dimensional coordinate system (not shown) associated with imager 206. Processor 204 superimposes mapping path 122 on operational image 250, thereby producing a superimposed operational image 270. Processor 204 directs display 210 to display superimposed operational image 270.

Radiopaque marker 214 is made of a material (e.g., barium sulfate, metal), which is opaque to an imaging medium employed by imager 206, such as sound waves, electromagnetic waves (e.g., X-ray), and the like. Therefore, radiopaque marker 214 is visible in operational image 250. The surgeon can observe an image 252 of radiopaque marker 214 within operational image 250, and within superimposed operational image 270.

When radiopaque marker 214 reaches origin 124, the surgeon may input a reset command to processor 204, via pointing device 208, to reset a distance of travel (not shown) measured by traveled length detector 202. The surgeon advances medical catheter 212 within tubular organ 118, substantially along mapping path 122 toward a region of interest (not shown) of the body of the patient. Traveled length detector 202 measures and outputs the distance traveled by medical catheter 212, within tubular organ 118 relative to origin 124. It is noted, that processor 204 may correct the output (i.e., the distance measurement) of traveled length detector 202 whenever the path of medical catheter 212 deviates from the path of mapping path 122 (i.e., by fault of the surgeon or of other factors) by compensation methods known in the art.

As the surgeon advances medical catheter 212 within tubular organ 118, processor 204 estimates a current position of distal portion 216 within tubular organ 212, according to the output of traveled length detector 202, and according to calculated distances between mapping positions 120 (FIG. 1B) from origin 124, along mapping path 122. Processor 204 superimposes a representation of previous positions 280, on superimposed operational image 270 and directs display 210 to display superimposed operational image 270.

IVUS imager 220 acquires one or more images (not shown) of an inner wall (not shown) of tubular organ 118, during a forward movement of medical catheter 212 from the point of entry of medical catheter 212 into the body of the patient, toward the region of interest. Alternatively, IVUS imager 220 acquires the images during pull-back of medical catheter 212 from the region of interest, toward the point of entry of medical catheter 212 into the body of the patient.

Figure 3:
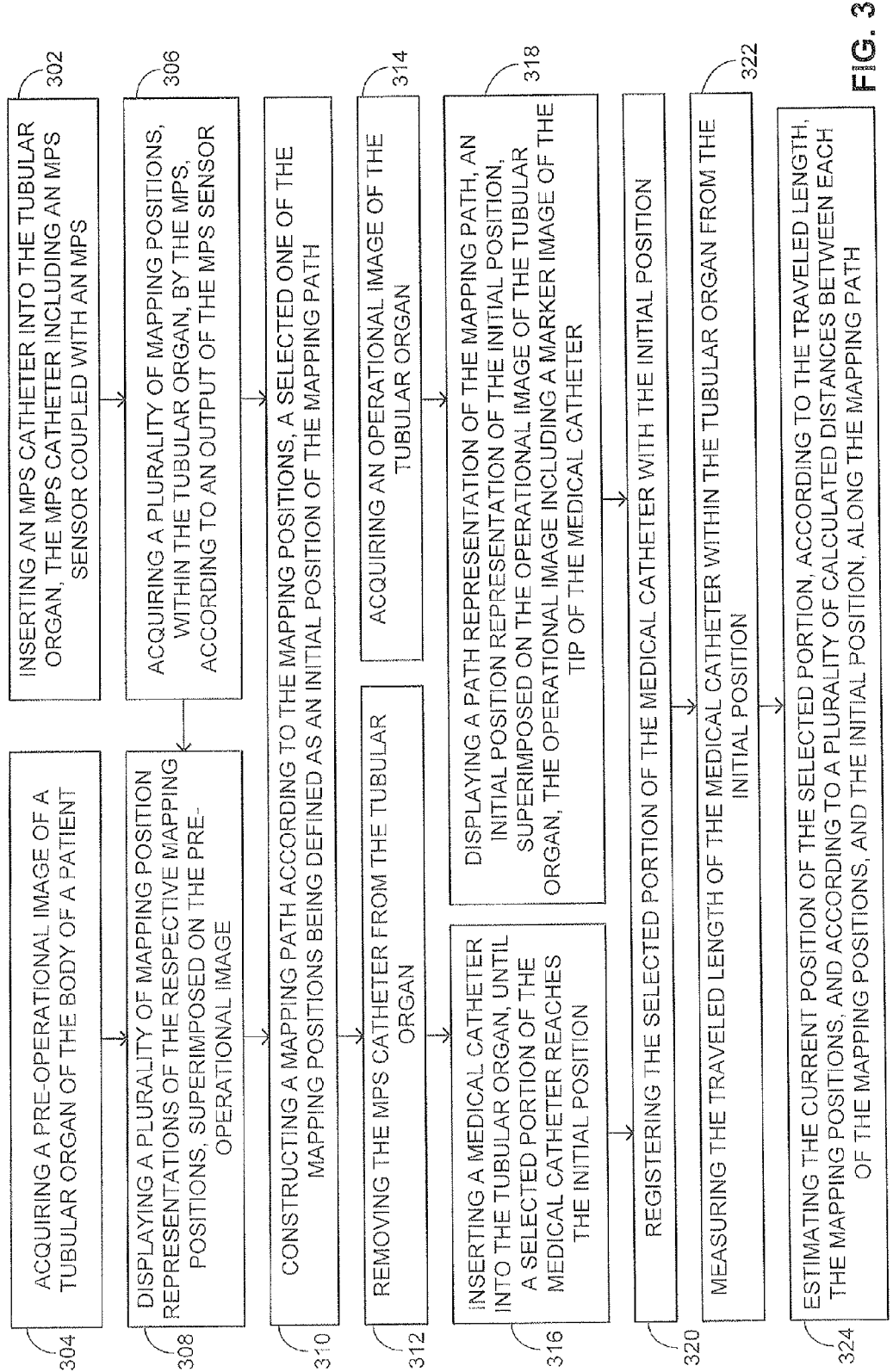
FIG. 3 is a schematic illustration of a method for operating the systems of FIGS. 1A, 1B, 2A, and 2B, operative in accordance with a further embodiment of the disclosed technique.

Reference is now made to FIG. 3, which is a schematic illustration of a method for operating the systems of FIGS. 1A, 1B, 2A, and 2B, operative in accordance with a further embodiment of the disclosed technique. In procedure 302, an MPS catheter is inserted into the tubular organ, the MPS catheter including an MPS sensor associated with an MPS. With reference to FIGS. 1A and 1B, MPS catheter 112 is inserted into tubular organ 118. MPS catheter 112 includes an MPS sensor 114 at distal portion 116 of MPS catheter 112. MPS sensor 114 is associated with MPS 102.

In procedure 304, a pre-operational image of the tubular organ of the body of a patient is acquired by an imager. With reference to FIGS. 1A and 1B, imager 106 acquires pre-operational image 150 of tubular organ 118.

In procedure 306, a plurality of mapping positions are acquired by the MPS, according to an output of the MPS sensor. With reference to FIGS. 1A and 1B, MPS sensor 114 acquires mapping positions 120, respective of the respective position of distal portion 116.

In procedure 308, a plurality of mapping position representations of the respective mapping positions are superimposed on the pre-operational image. With reference to FIGS. 1A, and 1B, processor 104 superimposes mapping positions 120 on operational image 150 (not shown), thereby producing superimposed operational image 170.

In procedure 310, a mapping path is constructed according to mapping positions, whereby a selected one of the mapping positions is defined as an initial position (i.e., an origin) of the mapping path. With reference to FIGS. 1A and 1B, MPS 102 determines the position of each of mapping positions 120, and processor 104 constructs mapping path 112 of the trajectory of distal portion 116 of MPS catheter 112, within tubular organ 118. The surgeon determines the initial position 124 of mapping path 122 by employing pointing device 108.

In procedure 312 the MPS catheter is removed from the tubular organ. With reference to FIG. 1A, the surgeon removes MPS catheter 112 from tubular organ 118.

In procedure 314, an operational image of the tubular organ is acquired. With reference to FIGS. 2A and 2B, imager 206 acquires operational image 250 of tubular organ 118. It is noted that in an intermediate procedure (not shown), which can follow procedure 314, the operational image 250 is registered with pre-operational image 150.

It is further noted, that the following procedures (i.e., procedure 316 and procedure 318) may typically be executed simultaneously. In procedure 316, a medical catheter is inserted into the tubular organ, until the selected portion of the medical catheter reaches the initial position. With reference to FIGS. 2A and 2B, the surgeon inserts medical catheter 212 into tubular organ 118, until the selected portion (e.g., marked by radiopaque marker 214) reaches initial position 124 by viewing image 252 of radiopaque marker 214 on superimposed operational image 270.

In procedure 318, a path representation of the mapping path, and an initial position representation of the initial position are displayed, superimposed on the operational image of the tubular organ, the operational image including a marker image of the tip of the medical catheter. With reference to FIGS. 2A and 2B, display 210 displays superimposed operational image 270. Superimposed operation image 270 includes illustrates a path representation of mapping path 122, an initial position representation of initial position 124, and marker image 252 of radiopaque marker 214.

In procedure 320, the selected portion (e.g., the tip) of the medical catheter is registered with the initial position. With reference to FIGS. 2A and 2B, the surgeon registers via pointing device 208 the selected portion (e.g., radiopaque marker 214) with initial position 124.

In procedure 322, the traveled length of the medical catheter within the tubular organ is measured from the initial position. With reference to FIGS. 2A and 2B, traveled length detector 202 measures and outputs the traveled length of medical catheter 212 within tubular organ 118, relative to initial position 124.

In procedure 324, the current position of the selected portion of the medical catheter is estimated, according to the traveled length, the mapping positions, and according to the plurality of calculated distances between each of the mapping positions and the initial position along the mapping path. With reference to FIGS. 2A and 2B, processor 204 determines an estimate of the current position of the selected portion (e.g., distal portion 216), according to the output of traveled length detector 202, and according to mapping positions 120 (FIG. 1B). Processor 204 superimposes previous position 280 of distal portion 216, on superimposed operational image 270. Processor 204 directs display 210 to display superimposed operational image 270.

According to another aspect of the disclosed technique, the system further includes an organ monitor coupled with the processor. The organ monitor acquires an organ timing signal of an organ of the patient. The processor gates the image acquired by the imager (e.g., a real-time image, a cine-loop), with the respective organ timing signal of the organ. The display displays a representation of the current position as well as previous positions of a selected portion (e.g., the distal portion or the tip) of the medical catheter, on the respective operational image, associated with the respective organ timing signal. In this manner, the surgeon can observe the representation of the tip of the medical catheter on an image of the tubular organ, which corresponds to the current position of the tip, respective of the current activity state of the organ. The organ monitor can monitor the timing signals of different organs of the body of the patient, which can cause the tubular organ in the respective organ such as the heart, lungs, and the like, to move in the corresponding cycles.

Figure 4A:
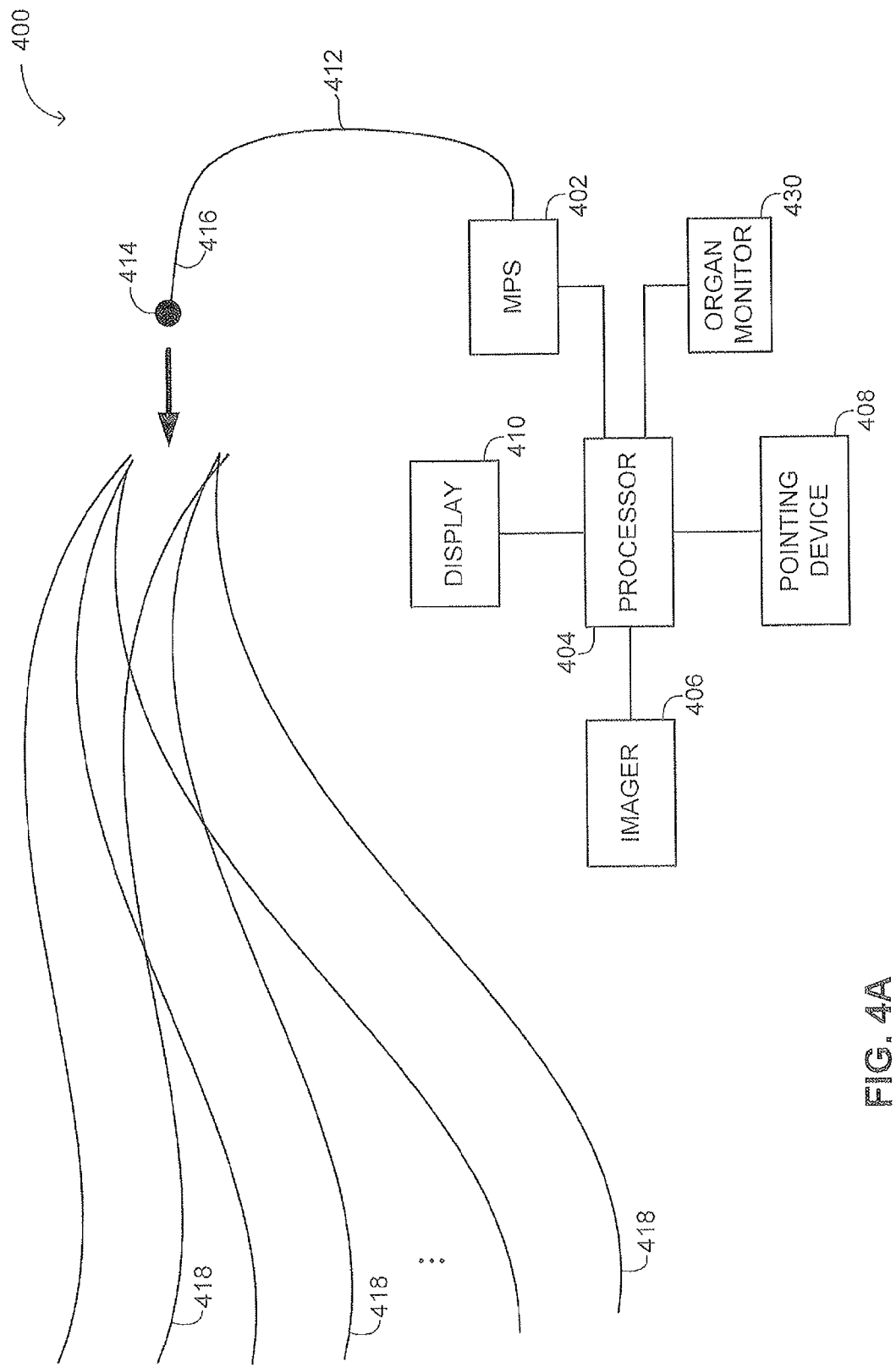
FIG. 4A is a schematic illustration of a system for producing a multi-state mapping path of a trajectory of an MPS catheter, within a tubular organ of the body of a patient, constructed and operative in accordance with another embodiment of the disclosed technique.
Figure 4C:
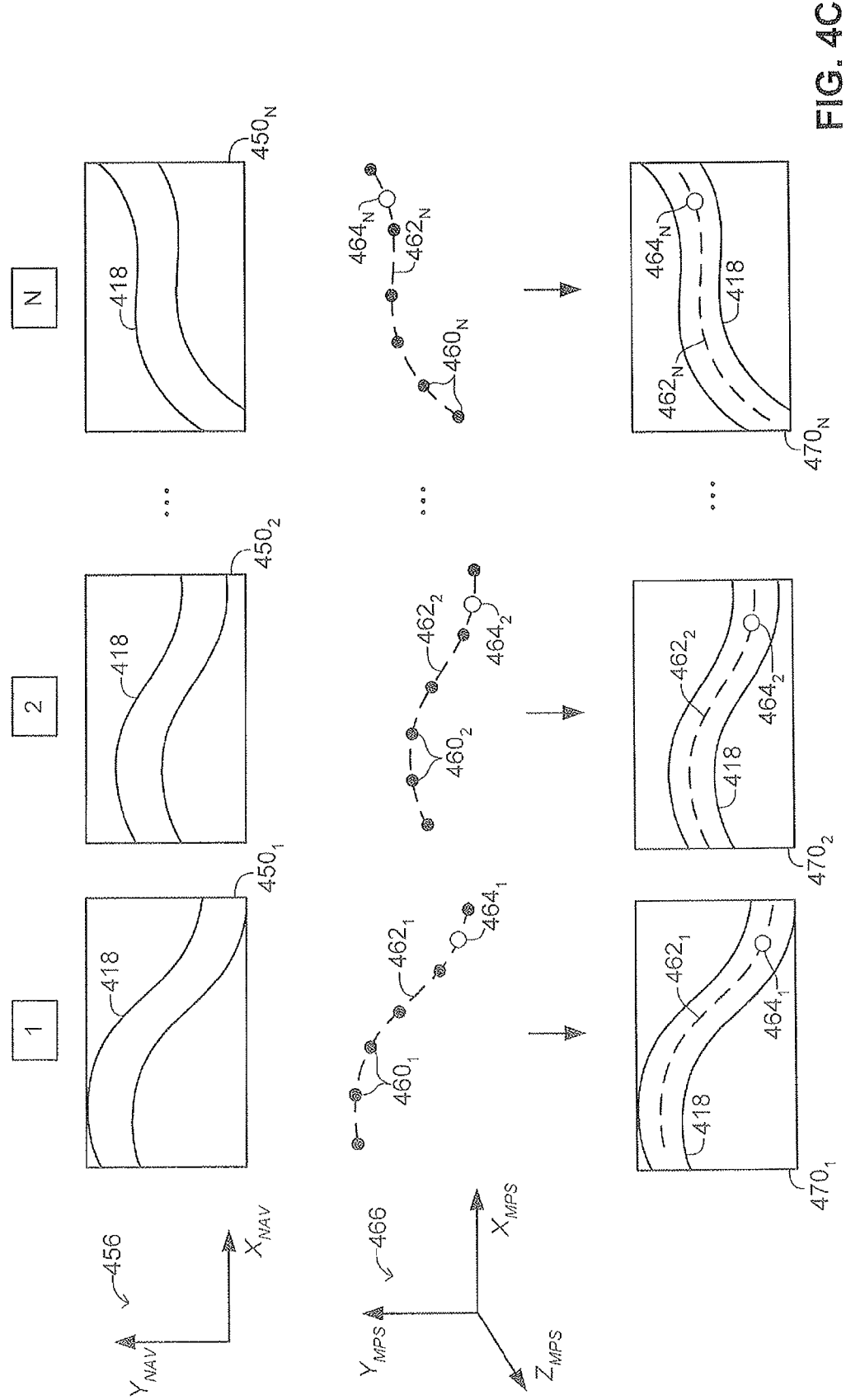
FIG. 4C is a schematic illustration of a superimposition of the multi-state mapping path of the trajectory of the MPS catheter of FIG. 4A, on a plurality of pre-operational images.

Reference is now made to FIGS. 4A, 4B and 4C. FIG. 4A is a schematic illustration of a system, generally referenced 400, for producing a multi-state mapping path of a trajectory of an MPS catheter, within a tubular organ of the body of a patient, constructed and operative in accordance with another embodiment of the disclosed technique. FIG. 4B is a schematic illustration of an organ timing signal of an organ of a patient and representative points in the organ timing signal. FIG. 4C is a schematic illustration of a superimposition of the multi-state mapping path of the trajectory of the MPS catheter of FIG. 4A, on a plurality of pre-operational images.

System 400 includes an MPS 402, a processor 404, an imager 406, a pointing device 408, a display 410, an MPS catheter 412, an MPS sensor 414, memory (not shown), and an organ monitor 430. MPS sensor 414 is located at a distal portion 416 of MPS catheter 412. Processor 404 is coupled with MPS 402, imager 406, pointing device 408, display 410, organ monitor 430, and with the memory. MPS 402 is coupled with MPS sensor 414, via an electric conductor. Alternatively, MPS 402 is coupled with MPS sensor 414, via a wireless link.

Organ monitor 430 is a device which acquires an organ timing signal 440 (FIG. 4B) of the organ of the patient (i.e., a signal representing the activity state of the organ, such as phases or states of the heart). Organ monitor 430 can be an electrocardiogram (ECG), a pulse monitor, a respiration monitor, and the like.

Imager 406 acquires a plurality of pre-operational images $450_1$, $450_2$, and $450_N$ (FIG. 4C) of a tubular organ 418. Each of pre-operational images $450_1$, $450_2$, and $450_N$ is associated with respective points $442_1$ (FIG. 4B), $442_2$, and $442_N$ in a cycle of organ timing signal 440. Pre-operational image $450_1$ is associated with point $442_1$ in the cycle of organ timing signal 440. Pre-operational image $450_2$ is associated with point $442_2$ in the cycle of organ timing signal 440. Pre-operational image $450_N$ is associated with point $440_N$ in the cycle of organ timing signal 440. Alternatively, imager 406 acquires a single real-time pre-operational image (not shown). It is noted that tubular organ 418 (FIG. 4A) is depicted by multiple representations thereof, which represent the movement of tubular organ 418 during the various states of the organ cycle.

A three-dimensional coordinate system 466 associated with MPS 402 is registered with a two-dimensional coordinate system 456 associated with each of pre-operational images $450_1$, $450_2$, and $450_N$. Alternatively, three-dimensional coordinate system 466 is registered with a two-dimensional coordinate system (not shown) associated with imager 406. During a mapping session, prior to a medical operation on the body of the patient, a surgeon (not shown) inserts MPS catheter 412 into tubular organ 418, until distal portion 414 of MPS catheter 412 enters an FOV of imager 406.

As the surgeon advances MPS catheter 412 into tubular organ 418, MPS 402 detects the position of MPS sensor 414, located substantially at a distal portion 416 of MPS catheter 412, according to an output of MPS sensor 414. MPS 402 acquires a plurality of mapping positions $460_1$, $460_2$, and $460_N$ (FIG. 4C), respective of the position of distal portion 416, during a forward movement of MPS catheter 412, from the point of entry (not shown) of MPS catheter 412 toward the region of interest. Alternatively, MPS 402 acquires mapping positions $460_1$, $460_2$ and $460_N$ during pull-back of MPS catheter 412, from the region of interest toward the point of entry. Mapping positions $460_1$, $460_2$ and $460_N$ are classified into groups of mapping positions, each group of mapping positions being associated with a specific point in the cycle of the organ timing signal. A plurality of mapping positions $460_1$ belong to a group 1 (FIGS. 4B and 4C) associated with point $442_1$ in organ timing signal 440. A plurality of mapping positions $460_2$ belong to a group 2 (FIGS. 4B and 4C) associated with point $442_2$ in organ timing signal 440. A plurality of mapping positions $460_N$ belong to a group N (FIGS. 4B and 4C) associated with point $442_N$ in organ timing signal 440. Each mapping position in a particular group of mapping positions is acquired at the same point in the cycle of organ timing signal 440. For example, each mapping position $460_1$ is acquired at the same point $442_1$, in the cycle of organ timing signal 440, (i.e., once the cycle repeats, in a repetitive cyclic organ timing signal, the next mapping position is acquired).

MPS 402 registers each mapping position in a particular group of mapping positions with respective two-dimensional coordinates in the respective pre-operational image. For example, MPS 402 registers each mapping position of mapping positions $460_1$ with respective two-dimensional coordinates in pre-operational image $450_1$.

Mapping positions $460_1$, $460_2$, and $460_N$ define a multi-state mapping path similar to mapping path 122 (FIG. 2B). Each group of mapping positions defines a mapping path of the multi-state mapping path, corresponding to the respective point in the organ timing signal of the organ. Processor 402 produces a mapping path $462_1$ from mapping positions $460_1$. Mapping path $462_1$ is an approximate representation of the trajectory (not shown) of the movement of distal portion 416 of distal portion 416 of MPS catheter 412, within tubular organ 418, at point $442_1$ in the cycle of organ timing signal 440. Processor 402 produces a mapping path $462_2$ from mapping positions $460_2$. Mapping path $462_2$ is an approximate representation of the trajectory (not shown) of the movement of distal portion 416 of MPS catheter 412, within tubular organ 418, at point $442_2$ in the cycle of organ timing signal 440. Processor 402 produces a mapping path $462_N$ from mapping positions $460_N$. Mapping path $462_N$ is an approximate representation of the trajectory (not shown) of the movement of distal portion 416 of MPS catheter 412, within tubular organ 418, at point $442_N$ in the cycle of organ timing signal 440. The memory stores mapping paths $462_1$, $462_2$, and $462_N$.

The surgeon determines a single initial position (not shown) of all of mapping paths $462_1$, $462_2$, and $462_N$, typically one of mapping positions $460_1$, $460_2$, and $460_N$, or alternatively, a physical point on the body of the patient, and the like. Further alternatively, the surgeon can determine a plurality of origins $464_1$, $464_2$, and $464_N$ (FIG. 4C) of the respective mapping paths $462_1$, $462_2$, and $462_N$. Each of origins $464_1$, $464_2$, and $464_N$ are reference points, which can be for example, points on respective mapping paths $462_1$, $462_2$, and $462_N$, one of respective mapping positions $460_1$, $460_2$, and $460_N$, a physical point on the body of the patient (e.g., marked by the surgeon), and the like. Each origin $464_1$, $464_2$ and $464_N$ is associated with the respective point in the cycle of organ timing signal 440. For example, origin $464_1$ is associated with point $442_1$ within the cycle of organ timing signal 440. Alternatively, each origin $464_1$, $464_2$, and $464_N$ is associated, respectively, with mapping paths $462_1$, $462_2$, and $462_N$. The surgeon selects the initial position, or alternatively, origins $464_1$, $464_2$, and $464_N$, by employing pointing device 408 (FIG. 4A).

Processor 404 superimposes mapping path $462_1$ on pre-operational image $450_1$, thereby producing a superimposed pre-operational image $470_1$. Processor 404 superimposes mapping path $462_2$ on pre-operational image $450_2$, thereby producing a superimposed pre-operational image $470_2$. Processor 404 superimposes mapping path $462_N$ on pre-operational image $450_N$, thereby producing a superimposed pre-operational image $470_N$. Display 410 displays superimposed pre-operational images $470_1$, $470_2$, and $470_N$. Superimposed pre-operational images $470_1$, $470_2$, and $470_N$ are synchronized (i.e., gated) with organ timing signal 440, and are displayed on display 410 at a display rate, which is substantially equal or greater than the cycle time of organ timing signal 440, unless imager 406 acquires all except one of pre-operational images $450_1$, $450_2$, and $450_N$ at some point in the phase of the organ which is aperiodic, due to abnormal rhythms of the organ (e.g., arrhythmia in the heart).

Figure 5A:
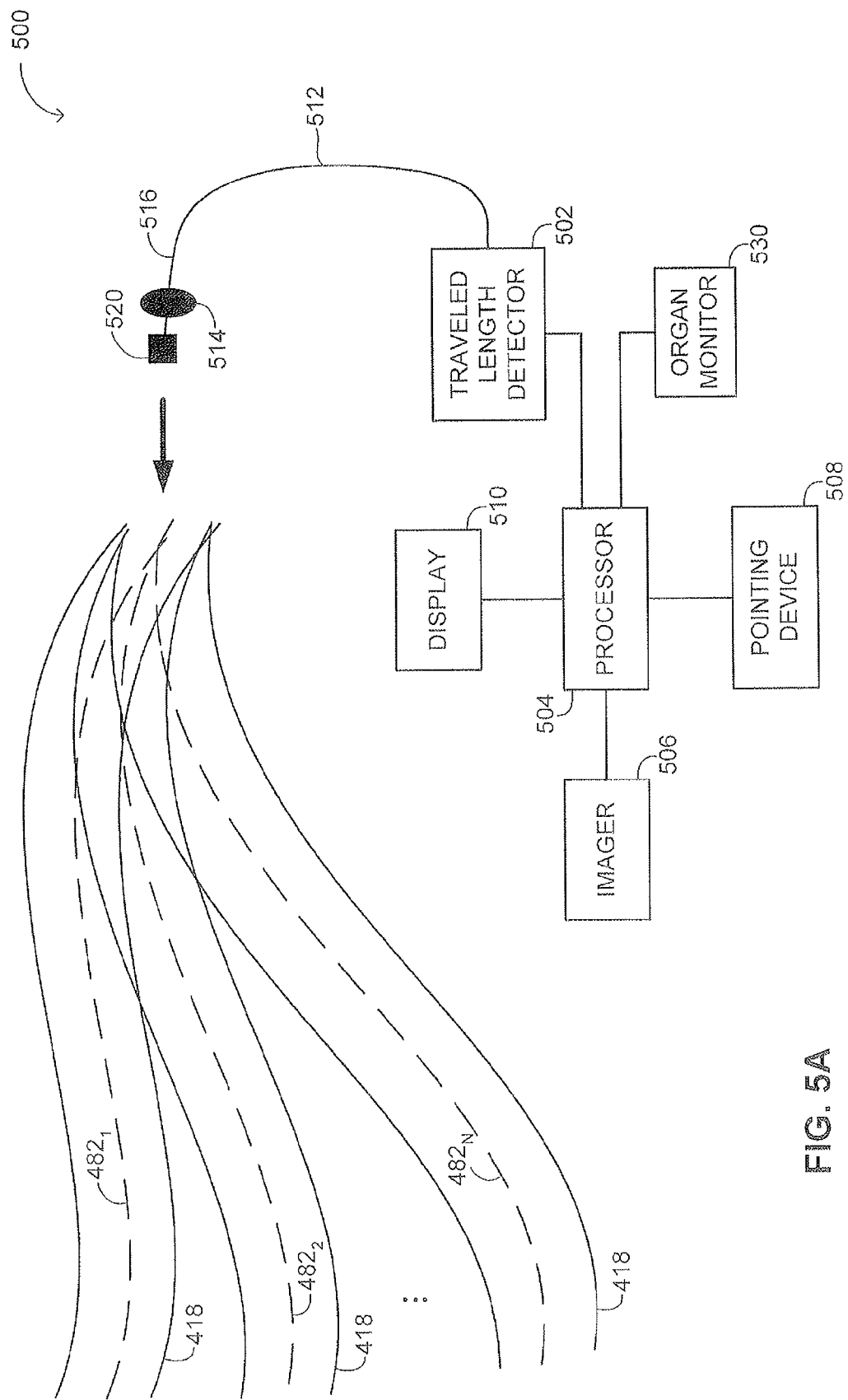
FIG. 5A is a schematic illustration of a system for determining the position of the tip of a medical catheter, within a tubular organ of the body of a patient, constructed and operative in accordance with a further embodiment of the disclosed technique.
Figure 5B:
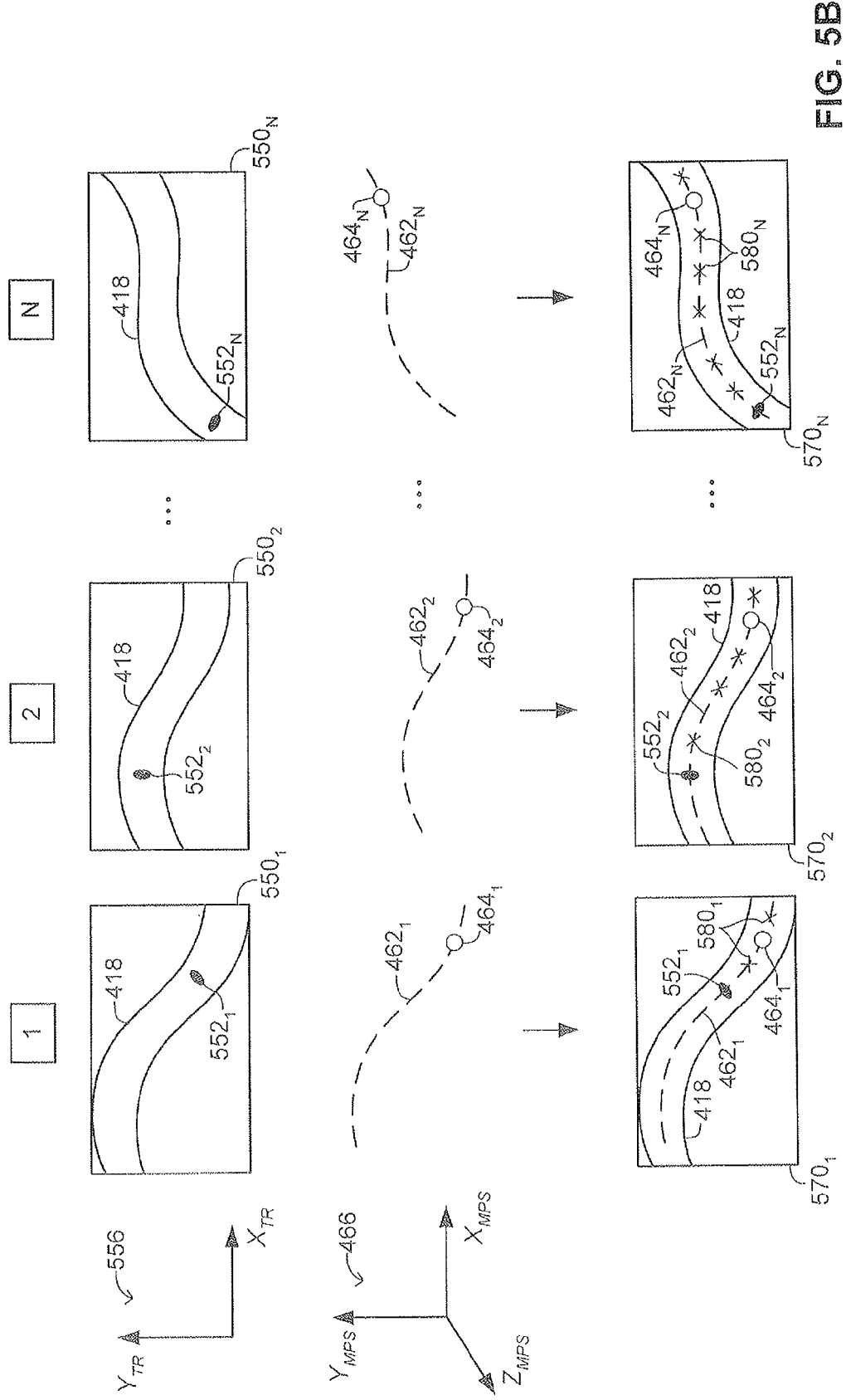
FIG. 5B is a schematic illustration of a multi-state mapping path of a trajectory of the MPS catheter of the system of FIG. 5A, superimposed on a operational image of the tubular organ of the patient.

Reference is now made to FIGS. 4B, 5A and 5B. FIG. 5A is a schematic illustration of a system, generally referenced 500, for determining the position of the tip of a medical catheter, within a tubular organ of the body of a patient, constructed and operative in accordance with a further embodiment of the disclosed technique. FIG. 5B is a schematic illustration of a multi-state mapping path of a trajectory of the MPS catheter of the system of FIG. 5A, superimposed on an operational image of the tubular organ of the patient.

System 500 includes a traveled length detector 502, a processor 504, an imager 506, a pointing device 508, a display 510, a medical catheter 512, a radiopaque marker 514, an IVUS imager 520, a memory (not shown), and an organ monitor 530. Radiopaque marker 514 and IVUS imager 520 are located substantially at a distal portion 516 of medical catheter 512. Processor 504 is coupled with traveled length detector 502, imager 506, pointing device 508, display 510, organ monitor 530, and with the memory. Traveled length detector 502 is coupled with medical catheter 512. Traveled length detector 502, processor 504, imager 506, pointing device 508, and display 510, are similar to traveled length detector 202 (FIG. 2A), processor 404 (FIG. 4A), imager 406, pointing device 408, and display 410, respectively.

During medical operation on the body of the patient, the surgeon inserts medical catheter 512 into tubular organ 418, until radiopaque marker 514 of medical catheter 512 is within the FOV of imager 506. The surgeon advances medical catheter 512 into tubular organ 418, and imager 506 acquires a plurality of operational images $550_1$, $550_2$, and $550_N$ (FIG. 5B) until radiopaque marker 514 reaches the initial position. The initial position can be one of the mapping positions, an activity-state specific origin (i.e., one of origins $464_1$, $464_2$, and $464_N$), corresponding to one of points $442_1$, $442_2$, $442_N$ (FIG. 4B), respectively, and the like. It is noted that each of operational images $550_1$, $550_2$, and $550_N$ is a real-time image of tubular organ 418. Alternatively, each of operational images $550_1$, $550_2$, and $550_N$, can be an image which is previously acquired.

Radiopaque marker 514 is made of a material that is visible in operational images $550_1$, $550_2$, and $550_N$ of tubular organ 418. The surgeon can observe images $552_1$, $552_2$, and $552_N$ of radiopaque marker 514, in operational images $550_1$, $550_2$, and $550_N$ (FIG. 5B), respectively.

Operational images $550_1$, $550_2$, and $550_N$ are associated with points $442_1$, $442_2$, and $442_N$ (FIG. 4B), respectively, in a cycle of organ timing signal 440. Operational image $550_1$ is associated with point $442_1$ in a cycle of organ timing signal 440. Operational image $550_2$ is associated with point $442_2$ in the cycle of organ timing signal 440. Operational image $550_N$ is associated with point $442_N$ in the cycle of organ timing signal 440.

A three-dimensional coordinate system 466 associated with MPS 402 is registered with a two-dimensional coordinate system 556 associated with operational images $550_1$, $550_2$, and $550_N$. Alternatively, three-dimensional coordinate system 466 is registered with a two-dimensional coordinate system (not shown) associated with imager 506.

Processor 504 superimposes each of mapping paths $462_1$, $462_2$, and $462_N$ on operational images $550_1$, $550_2$, and $550_N$, respectively, thereby producing superimposed operational images $570_1$, $570_2$, and $570_N$, respectively. Thus, processor 504 superimposes mapping path $462_1$ on operational image $550_1$, thereby producing a superimposed operational image $570_1$. Processor 504 superimposes mapping path $462_2$ on operational image $550_2$, thereby producing a superimposed operational image $570_2$. Processor 504 superimposes mapping path $462_N$ on operational image $550_N$, thereby producing a superimposed operational image $570_N$. Display 510 displays superimposed operational images $570_1$, $570_2$, and $570_N$.

When radiopaque marker 514 reaches the initial position (i.e., an activity-state specific origin, such as one of origins $464_1$, $464_2$, and $464_N$), the surgeon inputs a reset command to processor 504, by employing pointing device 508, to reset a distance of travel (not shown) of traveled length detector 502. The surgeon advances medical catheter 512 within tubular organ 418 substantially along a superposition (or a combination) of mapping paths $462_1$, $462_2$, and $462_N$ toward the region of interest of the body of the patient. A combination of mapping paths is formed from mapping paths $462_1$, $462_2$, and $462_N$ corresponding to groups of points respective of points $442_1$, $442_2$, and $442_N$, respectively, in organ timing signal 440.

Traveled length detector 502 measures and outputs the travel of medical catheter 512 within tubular organ 418 relative to the initial position. It is noted, that processor 504 may correct the output (i.e., the distance measurement) of traveled length detector 502 whenever the path of medical catheter 512 deviates from the path of each MPS paths $462_1$, $462_2$, and $462_N$ (i.e., by fault of the surgeon or by other factors) by compensation methods known in the art.

As the surgeon advances medical catheter 512 within tubular organ 418, processor 504 estimates the current position (not shown), of distal portion 516 within tubular organ 512, according to the output of traveled length detector 502, and according to mapping positions $562_1$, $562_2$, and $562_N$, respectively. Processor 504 superimposes a representation of each of previous positions $580_1$, $580_2$, and $580_N$, on superimposed operational images $570_1$, $570_2$, and $570_N$, respectively. Display 510 displays superimposed operational images $570_1$, $570_2$, and $570_N$ in a real-time sequenced manner. The processor 504 can direct display 510 to display a playback of superimposed operational images $570_1$, $570_2$, and $570_N$.

IVUS imager 520 acquires ultrasound images (not shown) of the region of interest, during a forward movement of medical catheter 512 from a point of entry of medical catheter 512 into the body of the patient toward the region of interest. Alternatively, IVUS imager 520 acquires the ultrasound images during pull-back of medical catheter 512 from region of interest toward the point of entry. Superimposed operational images $570_1$, $570_2$, and $570_N$ are synchronized (i.e., gated) with organ timing signal 440, and are displayed on display 510 at a display rate, which is substantially equal or greater than the cycle time of organ timing signal 440, unless the surgeon acquires all except one of operational images $550_1$, $550_2$, and $550_N$ at some point in the phase of the organ which is aperiodic (due to abnormal rhythms of the organ, e.g., arrhythmia in the heart).

Figure 6A:
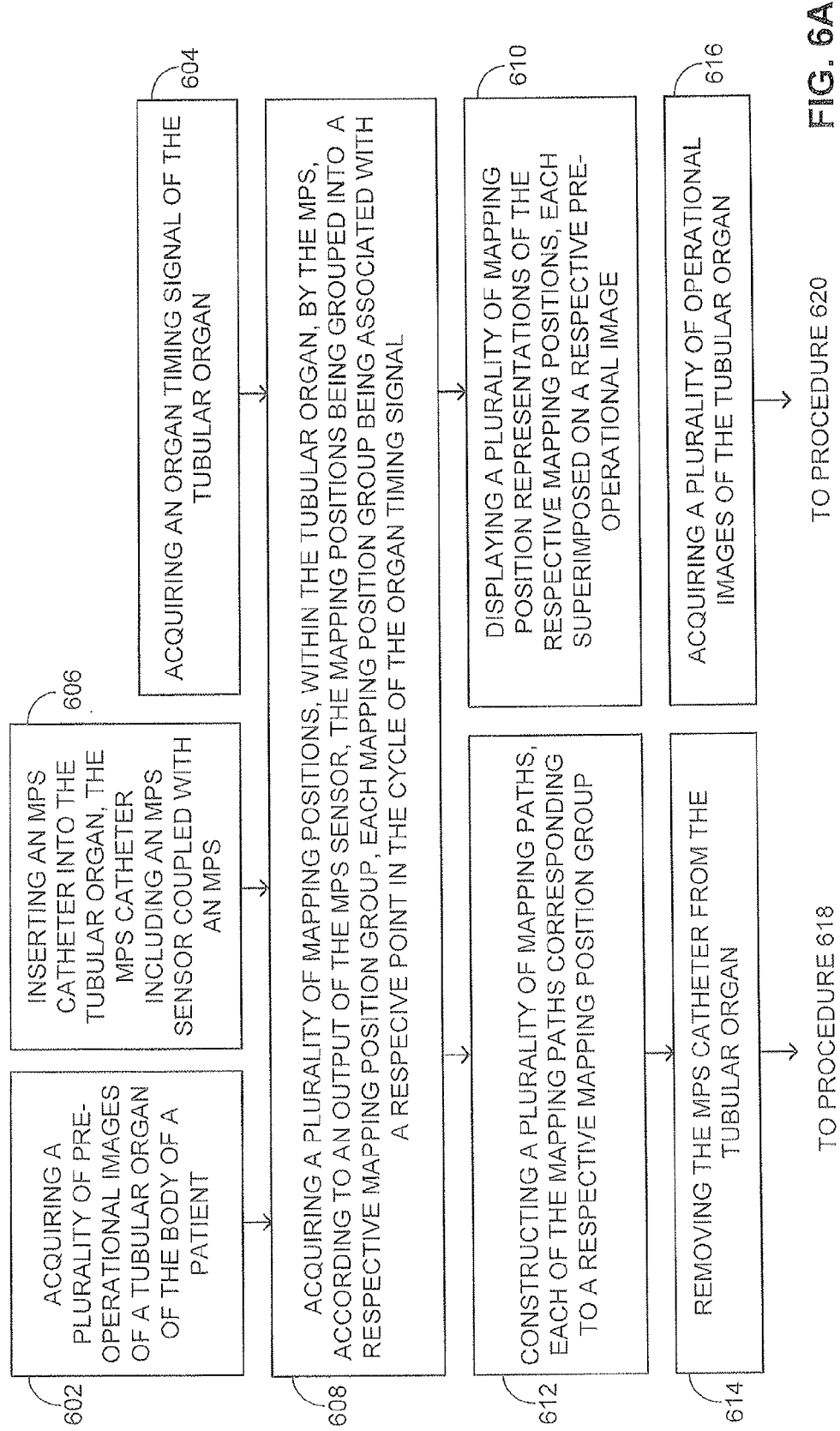
FIG. 6A is a schematic illustration of a method for operating the systems of FIGS. 4A, 4B, 4C 5A, and 5B, operative in accordance with another embodiment of the disclosed technique.
Figure 6B:
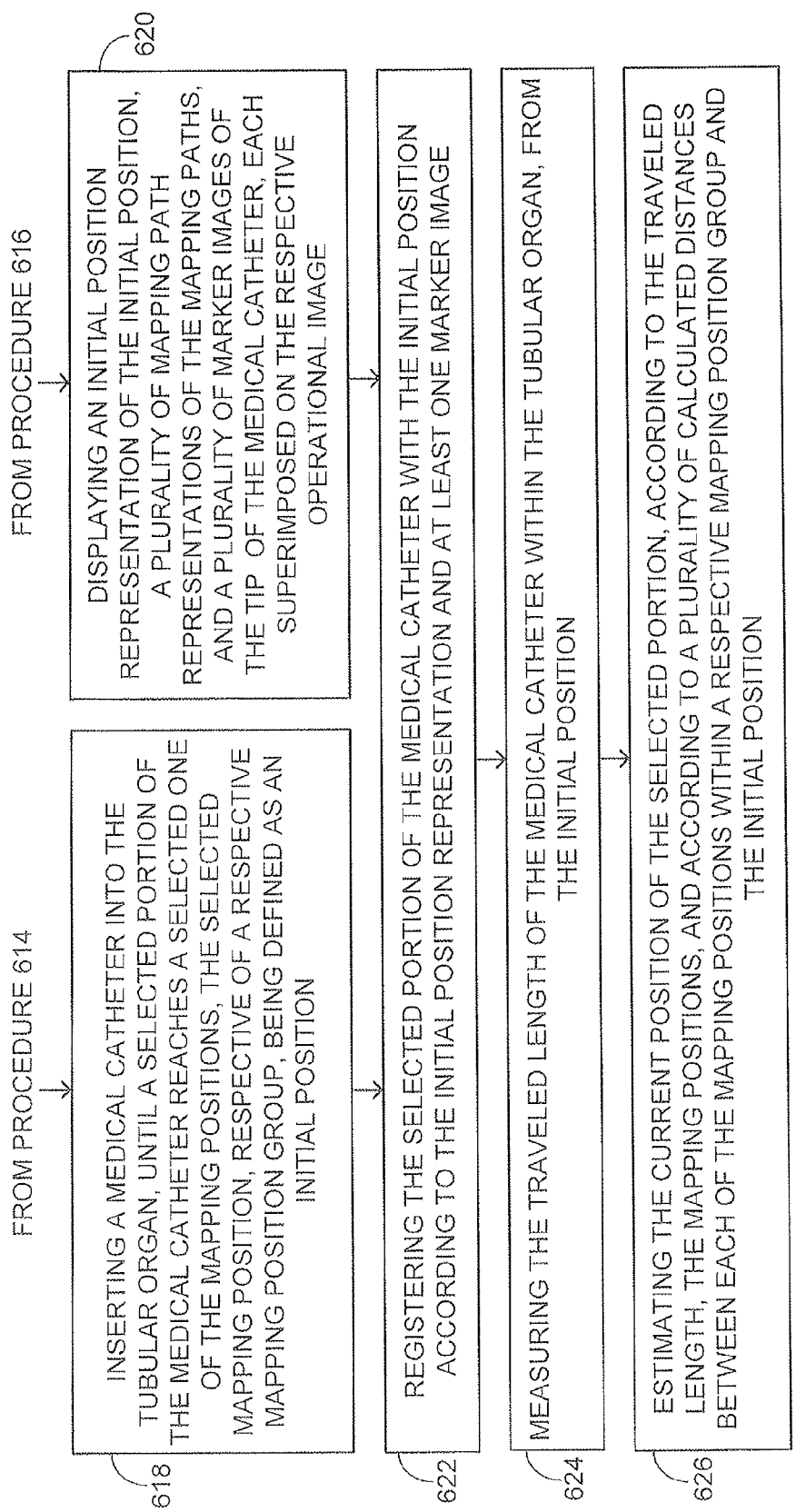
FIG. 6B is a schematic illustration of a continuation of the method of FIG. 6A.

Reference is now made to FIGS. 6A and 6B. FIG. 6A is a schematic illustration of a method for operating the systems of FIGS. 4A, 4B, 4C 5A, and 5B, operative in accordance with another embodiment of the disclosed technique. FIG. 6B is a schematic illustration of a continuation of the method of FIG. 6A.

In procedure 602, a plurality of pre-operative images of a tubular organ of the body of a patient are acquired by an imager. With reference to FIGS. 4A and 4C, imager 406 acquires pre-operational images $450_1$, $450_2$, and $450_N$ of tubular organ 418. Alternatively, imager 406 acquires a single real-time pre-operational image.

In procedure 604 (FIG. 6A), the organ timing signal of the tubular organ is acquired. With reference to FIGS. 4B and 5A, organ monitor 530 (FIG. 5A) is coupled (not shown) with tubular organ 418 and acquires organ timing signal 440 (FIG. 4B) of tubular organ 418.

In procedure 606, the MPS catheter is inserted into the tubular organ, the MPS catheter including an MPS sensor coupled with an MPS. With reference to FIG. 4A, MPS catheter 412 is inserted into tubular organ 418. MPS catheter 412 includes MPS sensor 414, which is coupled with MPS 402.

In procedure 608, a plurality of mapping positions within the tubular organ are acquired by the MPS according to an output of the MPS sensor. The mapping positions are grouped into a respective mapping position group, each mapping position group is associated with a respective point in the cycle of the organ timing signal. With reference to FIGS. 4A, 4B, and 4C, mapping positions $460_1$, $460_2$ and $460_N$ (FIG. 4C) are acquired by MPS 402 (FIG. 4A) according to the output of MPS sensor 414 (FIG. 4A). Mapping positions $460_1$, $460_2$ and $460_N$ are grouped into respective mapping groups $442_1$, $442_2$ and $442_N$ (FIG. 4B), whereby each mapping position group $442_1$, $442_2$ and $442_N$ is associated with a respective point (i.e., groups 1 through N illustrated in FIG. 4B) in the cycle of organ timing signal 440 (FIG. 4B).

In procedure 610, a plurality of mapping position representations of the respective mapping positions are displayed, each superimposed on a respective pre-operational image. With reference to FIGS. 4A and 4C, mapping positions $460_1$, $460_2$ and $460_N$ (FIG. 4C) are displayed on display 410 (FIG. 4A) each superimposed (not shown) on respective pre-operational images $470_1$, $470_2$ and $470_N$ (FIG. 4C).

In procedure 612, a plurality of mapping paths are constructed, each of the mapping paths corresponding to a respective mapping position group. With reference to FIGS. 4A and 4C, processor 404 constructs mapping paths $462_1$, $462_2$ and $462_N$ (FIG. 4C), each mapping path corresponding to a respective mapping position group (i.e., groups 1, 2, and N, respectively).

In procedure 614 the MPS catheter is removed from the tubular organ. With reference to FIG. 4A, the surgeon removes MPS catheter 412 from tubular organ 418.

It is noted that the following procedures (i.e., procedure 618 and procedure 620) are typically executed simultaneously. In procedure 618, a medical catheter is inserted into the tubular organ until a selected portion of the medical catheter reaches a selected one of the mapping positions. The selected mapping position corresponds to a respective mapping position group, and is defined as an initial position. With reference to FIGS. 4C, 5A and 5B, medical catheter 512 is inserted into tubular organ 418 until distal portion 516 (i.e., the selected portion) reaches one of mapping positions $460_1$, $460_2$ and $460_N$ (FIG. 4C). Alternatively, medical catheter 512 is inserted into tubular organ 418 until radiopaque marker 514 (FIG. 5A), located at distal portion 516 (FIG. 5A) reaches a respective one of origins $464_1$, $464_2$ and $464_N$ (FIG. 4C) of the respective group of mapping positions $460_1$, $460_2$ and $460_N$ (FIG. 4C). A selected mapping position is defined as the initial position (not shown). It is noted that that surgeon determines when radiopaque marker 514 reaches origin according to procedure 620.

In procedure 620, an initial position representation of the initial position, the plurality of mapping path representations of the mapping paths, and a plurality of marker images of the tip of the medical catheter are displayed, each superimposed on the respective operational image. With reference to FIGS. 5A and 5B, representations of mapping paths $462_1$, $462_2$ and $462_N$ (FIG. 5B) are displayed by display 510 (FIG. 5A), each respectively superimposed on operational images $550_1$, $550_2$ and $550_N$ (FIG. 5B) as superimposed operational images $570_1$, $570_2$ and $570_N$ (FIG. 5B), respectively. A representation of the initial position is superimposed (not shown) on superimposed operational images $570_1$, $570_2$ and $570_N$. Marker images $552_1$, $552_2$ and $552_N$ (FIG. 5B) of radiopaque marker 514 (FIG. 5A) are each displayed on the respective one of superimposed operational images $570_1$, $570_2$ and $570_N$.

It is noted that in an intermediate procedure (not shown), which can follow procedure 620, each of operational images $550_1$, $550_2$, and $550_N$ of tubular organ 418 are registered with each of pre-operational images $450_1$, $450_2$, and $450_N$, respectively.

In procedure 622, the selected portion of the medical catheter is registered with the initial position according to the initial position representation and the at least one marker image. With reference to FIGS. 5A and 5B, the surgeon employs pointing device 508 (FIG. 5A) for selecting a registration situation, thereby registering the selected portion (e.g., radiopaque marker 514) with the initial position, according to the initial position representation (e.g., a selected one of origins $464_1$, $464_2$ and $464_N$ in FIG. 5B), according to the initial position representation and at least one marker image (i.e., one of marker images $552_1$, $552_2$ and $552_N$).

In procedure 624, the traveled length of the medical catheter within the tubular organ is measured from the initial position. With reference to FIGS. 5A and 5B, traveled length detector 502 measures the traveled length of medical catheter 512 within tubular organ 418 relative to the initial position, and produces an output respective of the traveled length.

In procedure 624, the current position of the selected portion of the medical catheter is estimated, according to the measured travel length relative to the origin, the mapping positions, and according to a plurality of calculated distances between each of the mapping positions within a respective mapping position group and the initial position. With reference to FIGS. 5A and 5B, processor 504 estimates the current position of distal portion 516, according to the output of traveled length detector 502, and according to the mapping positions $460_1$, $460_2$, and $460_N$ (FIG. 4C). Processor 504 superimposes previous positions $580_1$, $580_2$, and $580_N$ of distal portion 516 on operational images $550_1$, $550_2$, and $550_N$, respectively, thereby producing superimposed operational images $570_1$, $570_2$, and $570_N$, respectively. Display 510 displays superimposed operational images $570_1$, $570_2$, and $570_N$ in a real-time sequenced manner. Alternatively, the processor can direct display 510 to display a playback of superimposed operational images $570_1$, $570_2$, and $570_N$.

It will be appreciated by persons skilled in the art that the disclosed technique is not limited to what has been particularly shown and described hereinabove. Rather the scope of the disclosed technique is defined only by the claims, which follow.

The invention claimed is:

1. A method for determining the current position of a selected portion of a medical catheter inserted into a tubular organ, the method comprising:
   acquiring a plurality of mapping positions of a Medical Positioning System (MPS) catheter within the tubular organ according to output from a sensor included on the MPS catheter, the sensor electrically coupled with an MPS;

displaying a mapping position representation of the mapping positions, superimposed on an image of the tubular organ;

constructing a mapping path according to the mapping positions, a selected one of the mapping positions being defined as an initial position of the mapping path;

displaying an operational image of the tubular organ, a path representation of the mapping path, and an initial position representation of the initial position superimposed on the operational image, and a marker image of the selected catheter position of the medical catheter, registering a selected catheter portion with the initial position when the selected catheter portion is disposed at the initial position;

measuring a traveled length of the catheter within the tubular organ from the initial position; and estimating a current three-dimensional position of the selected catheter portion according to the traveled length, according to the mapping positions, and according to a plurality of calculated distances between each of the mapping positions, and the initial position, along the mapping path.

2. The method according to claim 1, further comprising acquiring a pre operational image of the tubular organ, by an imager.

3. The method according to claim 2, further comprising registering a three-dimensional coordinate system associated with the MPS with a two-dimensional coordinate system associated with the pre operational image.

4. The method according to claim 1, further comprising acquiring an operational image of the tubular organ, after constructing the mapping path, to enable display of a representation of the at least one mapping path, on the operational image.

5. The method according to claim 4, further comprising superimposing the representation of the at least one mapping path on the operational image.

6. The method according to claim 5, further comprising displaying a superimposed operational image of the representation of the at least one mapping path on the operational image.

7. The method according to claim 1, further comprising registering the tip of the medical catheter with the initial position.

8. The method according to claim 1, further comprising acquiring an organ timing signal of an organ.

9. The method according to claim 8, further comprising acquiring a plurality of pre operational images of the organ, according to the organ timing signal.

10. The method according to claim 9, further comprising registering each of the mapping positions with respective two-dimensional coordinates of a respective pre operational image.

11. The method according to claim 8, further comprising grouping the mapping positions into respective mapping position groups, each of the mapping position groups being associated with a respective point in the organ timing signal.

12. The method according to claim 8, further comprising:
acquiring a plurality of pre operational images of the tubular organ; and
associating each of the pre operational images with a respective point in the organ timing signal.

13. A system for determining the position of a medical catheter within a tubular organ of a body of a patient, the system comprising:
a Medical Positioning System (MPS) including:
at least one electromagnetic field generator;
a Medical Positioning System (MPS) catheter;
a Medical Positioning System (MPS) sensor coupled with the MPS catheter; and
a Medical Positioning System (MPS) processor coupled with the at least one electromagnetic field generator and with the MPS sensor, the MPS processor determining the relative position of the MPS sensor from the at least one electromagnetic field generator;
a memory coupled with the MPS processor, the memory adapted to store a mapping path including an initial position;
a registerer for determining a registration situation of a selected portion of the medical catheter with the initial position;
a traveled length detector coupled with the medical catheter, the traveled length detector adapted to measure a traveled length of the medical catheter within the tubular organ, the traveled length being defined as a length of a mapping path of the selected portion of the medical catheter from the initial position; and
a processor coupled with the memory, with the registerer, and with the traveled length detector, the processor estimating the current three-dimensional position of the selected portion of the medical catheter according to the traveled length and according to calculated distances between the mapping positions from the initial position along the mapping path.

14. The system according to claim 13, further comprising an imager coupled with the processor, the imager acquiring the at least one pre operational image of the tubular organ.

15. The system according to claim 14, wherein the imager is selected from a list consisting of:
fluoroscope;
ultrasound;
C-arm;
computer tomography (CT) imager;
magnetic resonance imager (MRI);
positron emission tomography (PET) imager;
single photon emission computer tomography (SPECT) imager;
infrared image detector;
X-ray imager;
optical coherence tomography (OCT) imager; and
intracardiac echocardiogram (ICE).

16. The system according to claim 14, wherein the processor registers a three-dimensional coordinate system associated with the MPS with a two-dimensional coordinate system associated with the pre operational image.

17. The system according to claim 14, wherein the processor registers a three-dimensional coordinate system associated with the MPS with a two-dimensional coordinate system associated with the imager.

18. The system according to claim 14, wherein the processor is adapted to superimpose the representation of the at least one mapping path on the operational image.

19. The system according to claim 13 further comprising an organ monitor coupled with the processor, the organ monitor acquiring an organ timing signal of the tubular organ.

20. The system according to claim 19, wherein the imager acquires a plurality of pre operational images of the tubular organ, and wherein the processor further associates each of the pre operational images with a respective point in the organ timing signal.

21. The system according to claim 20, wherein the processor further registers each of the mapping positions with respective two-dimensional coordinates of a respective the pre operational image.

22. The method of claim 1, wherein the registering, the measuring, and the estimating are performed with the MPS catheter removed from the tubular organ.

\* \* \* \* \*